United States Patent [19]

Abraham et al.

[11] Patent Number: 5,731,454

[45] Date of Patent: *Mar. 24, 1998

[54] ALLOSTERIC MODIFIERS OF HEMOGLOBIN USEFUL FOR DECREASING OXYGEN AFFINITY AND PRESERVING OXYGEN CARRYING CAPABILITY OF STORED BLOOD

[75] Inventors: Donald J. Abraham, Midlothian; Gajanan Joshi, Richmond, both of Va.; Ramnarayan Randad, Frederick, Md.; Jayashree Panikker, Richmond, Va.

[73] Assignee: Virginia Commonwealth University, Richmond, Va.

[*] Notice: The term of this patent shall not extend beyond the expiration date of Pat. Nos. 5,382,680 and 5,432,191 and 5,122,539 and 5,290,803.

[21] Appl. No.: 374,206

[22] Filed: Jan. 18, 1995

Related U.S. Application Data

[63] Continuation-in-part of Ser. No. 101,501, Jul. 30, 1993, Pat. No. 5,432,191, which is a continuation-in-part of Ser. No. 6,246, Jan. 19, 1993, Pat. No. 5,290,803, which is a continuation-in-part of Ser. No. 722,382, Jun. 26, 1991, Pat. No. 5,382,680, which is a continuation-in-part of Ser. No. 702,947, May 20, 1991, Pat. No. 5,122,539, which is a continuation-in-part of Ser. No. 478,848, Dec. 12, 1990, Pat. No. 5,049,695, which is a continuation of Ser. No. 623,346, Dec. 7, 1990, abandoned.

[51] Int. Cl.$^6$ .................. C07C 229/04; C07C 229/34; C07C 229/42

[52] U.S. Cl. .................. 560/43; 560/43; 562/434; 562/455

[58] Field of Search .................. 560/43, 20; 562/455, 562/434

[56] References Cited

U.S. PATENT DOCUMENTS

| | | | |
|---|---|---|---|
| 5,122,539 | 6/1992 | Abraham et al. | 514/563 |
| 5,290,803 | 3/1994 | Abraham et al. | 514/421 |
| 5,382,680 | 1/1995 | Abraham et al. | 562/451 |
| 5,432,191 | 7/1995 | Abraham et al. | 514/421 |

*Primary Examiner*—Alan L. Rotman
*Attorney, Agent, or Firm*—Whitham, Curtis, Whitham & McGinn

[57] ABSTRACT

A family of compounds has been found to be useful for right-shifting hemoglobin towards a low oxygen affinity state. The compounds are capable of acting on hemoglobin in whole blood. In addition, the compounds can maintain the oxygen affinity in blood during storage and can restore the oxygen affinity of outdated blood.

10 Claims, 26 Drawing Sheets

5,731,454

ALLOSTERIC MODIFIERS OF HEMOGLOBIN USEFUL FOR DECREASING OXYGEN AFFINITY AND PRESERVING OXYGEN CARRYING CAPABILITY OF STORED BLOOD

CROSS-REFERENCE TO RELATED APPLICATIONS

This patent application is a continuation-in-part (CIP) application of Ser. No. 08/101,501, dated Jul. 30, 1993 and which issued as U.S. Pat. No. 5,432,191, which in turn is a C-I-P of Ser. No. 08/006,246 filed Jan. 19, 1993, now U.S. Pat. No. 5,290,803, which in-turn is a C-I-P of Ser. No. 07/722,382, filed Jun. 26, 1991, now U.S. Pat. No. 5,382,680, which in-turn is a C-I-P of Ser. No. 07/702,947 filed May 20, 1991, which in-turn is a C-I-P of Ser. No. 07/478,848 filed Dec. 12, 1990, U.S. Pat. No. 5,049,695, which in-turn is a continuation of Ser. No. 07/623,346 filed Dec. 7, 1990, now abandoned.

DESCRIPTION

BACKGROUND OF THE INVENTION

1. Field of the Invention

The present invention generally relates to using a family of compounds to adjust the allosteric equilibrium of hemoglobin toward a low oxygen affinity state. Moreover, the invention includes several new compounds and contemplates using the family of compounds for use in treating diseases involving oxygen deficiency, in wound healing, and in restoring oxygen affinity of stored blood.

2. Description of the Prior Art

Hemoglobin is a tetrameric protein which delivers oxygen via an allosteric mechanism. Oxygen binds to the four hemes of the hemoglobin molecule. Each heme contains porphyrin and iron in the ferrous state. The ferrous iron-oxygen bond is readily reversible. Binding of the first oxygen to a heme requires much greater energy than the second oxygen molecule, binding the third oxygen requires even less energy, and the fourth oxygen requires the lowest energy for binding. Hemoglobin has two α and two β subunits arranged with a two fold symmetry. The α and β dimers rotate during oxygen release to open a large central water cavity. The allosteric transition that involves the movement of the alpha-beta dimer takes place between the binding of the third and fourth oxygen. The $\alpha_1\beta_1$ interface binding is tighter than the $\alpha_1\alpha_2$ or $\alpha_1\beta_2$ interfaces.

In blood, hemoglobin is in equilibrium between two allosteric structures. In the "T" (for tense) state, hemoglobin is deoxygenated. In the "R" (for relaxed) state, hemoglobin is oxygenated. An oxygen equilibrium curve can be scanned, using well known equipment such as the AMINCO™ HEM—O—SCAN, to observe the affinity and degree of cooperativity (allosteric action) of hemoglobin. In the scan, the Y-axis plots the percent of hemoglobin oxygenation and the X-axis plots the partial pressure of oxygen in millimeters of mercury (mmHg). If a horizontal line is drawn from the 50% oxygen saturation point to the scanned curve and a vertical line is drawn from the intersection point of the horizontal line with the curve to the partial pressure X-axis, a value commonly known as the $P_{50}$ is determined (i.e., this is the pressure in mmHg when the scanned hemoglobin sample is 50% saturated with oxygen). Under physiological conditions (i.e., 37° C., pH=7.4, and partial carbon dioxide pressure of 40 mm Hg), the $P_{50}$ value for normal adult hemoglobin (HbA) is around 26.5 mmHg. If a lower than normal $P_{50}$ value is obtained for the hemoglobin under test, the scanned curve is considered to be "left-shifted" and the presence of high affinity hemoglobin is indicated. Conversely, if a higher than normal $P_{50}$ value is obtained for the hemoglobin under test, the scanned curve is considered to be "right-shifted" and the presence of low affinity hemoglobin is indicated.

It has been proposed that influencing the allosteric equilibrium of hemoglobin is a viable avenue of attack for treating diseases. The conversion of hemoglobin to a high affinity state is generally regarded to be beneficial in resolving problems with deoxy Hemoglobin-S (sickle cell anemia). The conversion of hemoglobin to a low affinity state is believed to have general utility in a variety of disease states where tissues suffer from low oxygen tension, such as ischemia and radio sensitization of tumors. Several synthetic compounds have been identified which have utility in the allosteric regulation of hemoglobin and other proteins. For example, several new compounds and methods for treating sickle cell anemia which involve the allosteric regulation of hemoglobin are reported in U.S. Pat. No. 4,699,926 to Abraham et al., U.S. Pat. No. 4,731,381 to Abraham et al., U.S. Pat. No. 4,731,473 to Abraham et al., U.S. Pat. No. 4,751,244 to Abraham et al., and U.S. Pat. No. 4,887,995 to Abraham et al. Furthermore, in both Perutz, "Mechanisms of Cooperativity and Allosteric Regulation in Proteins", *Quarterly Reviews of Biophysics* 22, 2 (1989), pp. 163–164, and Lalezari et al., "LR16, a compound with potent effects on the oxygen affinity of hemoglobin, on blood cholesterol, and on low density lipoprotein", *Proc. Natl. Acad. Sci.*, USA 85 (1988), pp. 6117–6121, compounds which are effective allosteric hemoglobin modifiers are discussed. In addition, Perutz et al. has shown that a known antihyperlipoproteinemia drug, bezafibrate, is capable of lowering the affinity of hemoglobin for oxygen (see, "Bezafibrate lowers oxygen affinity of hemoglobin", Lancet 1983, 881.

German Patent Applications 2,149,070 and 2,432,560, both to Witte et al., disclose compounds which are structurally similar to some of the compounds in the family of compounds defined by this invention. However, the Witte et al. patent applications contemplate use of the compounds for the reduction of serum lipid levels. The Witte et al. patent applications do not provide any indication of the potential use of the compounds for allosteric hemoglobin modification.

SUMMARY OF THE INVENTION

It is therefore an object of this invention to provide a method of using a family of compounds to allosterically modify hemoglobin such that the hemoglobin is present in blood in a lower oxygen affinity state.

It is another object of this invention to provide a method of prolonging the storage life of blood by adding compounds within a particular family of compounds to the blood.

It is another object of this invention to provide new compounds which are capable of allosterically modifying hemoglobin.

According to the invention, an allosteric hemoglobin modifying family of compounds is defined by the formula:

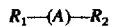

where $R_1$ and $R_2$ each are a substituted or unsubstituted aromatic or heteroaromatic compound, or substituted or unsubstituted alkyl or heteroalkyl ring compound, or a substituted or unsubstituted phthalimide compound, and where $R_1$ and $R_2$ may be the same or different, where A is a chemical bridge which includes two to four chemical moieties bonded together between $R_1$ and $R_2$, wherein said chemical moieties in A are selected from the group consisting of CO, O, S, $SO_2$, NH, $NR_3$ where $R_3$ is a $C_{1-6}$ alkyl group, $NR_4$ where $R_4$ includes two carbonyls as part of a phthalimide compound formed with $R_1$ or $R_2$, $CH_2$, CH, and C, with the caveat that, except in the case where A contains two identical CH and C moieties positioned adjacent one another to form an alkene or alkyne, the chemical moieties in A are each different from one another, and wherein at least one of $R_1$ or $R_2$ is substituted with a compound having the chemical formula:

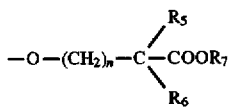

where n is zero to five, where $R_5$ and $R_6$ are selected from the group consisting of hydrogen, halogen, substituted or unsubstituted $C_{1-12}$ alkyl groups, and substituted or unsubstituted aromatic or heteroaromatic groups, and these moieties may be the same or different, or alkyl moieties of part of an aliphatic ring connecting $R_5$ and $R_6$, and where $R_7$ is a hydrogen, halogen, salt cation (e.g., sodium, potassium, ammonium, etc.), metal, or substituted or unsubstituted $C_{1-6}$ alkyl group.

Many compounds within this family have been synthesized and their effect on the $P_{50}$ value of hemoglobin has been determined. Each of the compounds tested was found to increase the $P_{50}$ value of hemoglobin; hence, the compounds are capable of driving the allosteric equilibrium of hemoglobin towards a condition favoring the low oxygen affinity state. In addition, the compounds were found to stabilize the degree of oxygen dissociation of hemoglobin in stored blood over extended periods of time. Furthermore, the compounds were found to be well tolerated by mice when administered as an intraperitoneal dose. Because the compounds within the family defined by this invention are capable of shifting the hemoglobin allosteric equilibrium toward the low affinity "T" state, they have the ability to cause hemoglobin to deliver more oxygen to tissues. Thus, the compounds of the invention should be valuable as antiischemic agents, as sensitizers for x-ray irradiation in cancer therapy, as wound healing agents, in treating disorders related to low oxygen delivery in the brain such as Alzheimer's, depression, and schizophrenia, in preparing blood substitutes, and in blood storage, as well as other applications.

BRIEF DESCRIPTION OF THE DRAWINGS

The foregoing and other objects, aspects and advantages will be better understood from the following detailed description of a preferred embodiment of the invention with reference to the drawings, in which:

FIGS. 1b and 1c are chemical structures defining two subsets of the family defined in FIG. 1a;

DETAILED DESCRIPTION OF THE PREFERRED EMBODIMENTS OF THE INVENTION

Figure 1A:
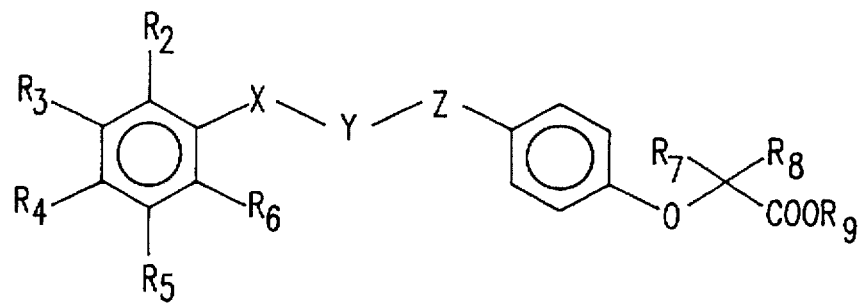
FIG. 1a is a chemical structure defining a particularly preferred group within the family of compounds used in the present invention.
Figure 1B:
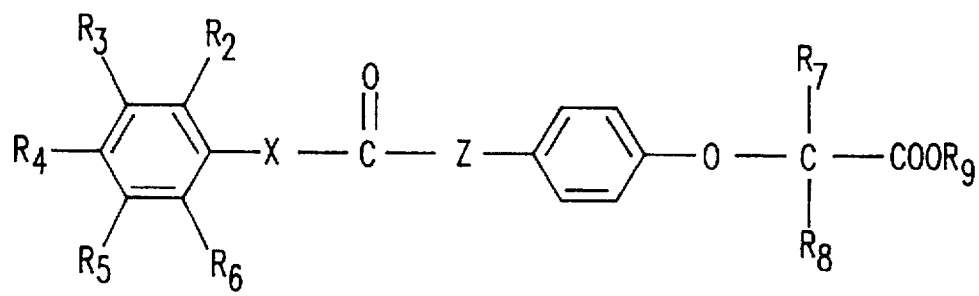
Figure 1C:
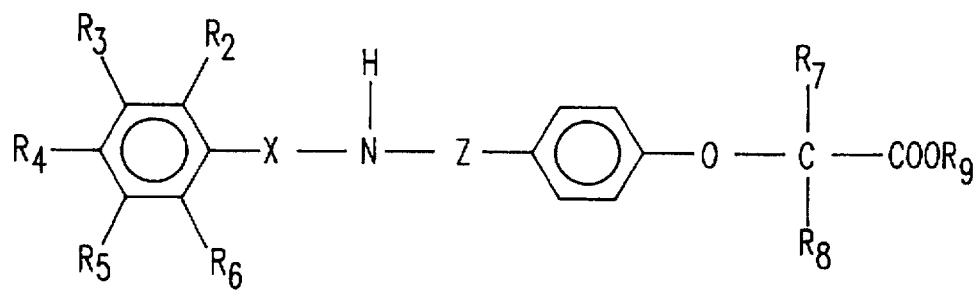

Referring now to the drawings and, more particularly, to FIGS. 1a–c which illustrate the general structural formula of particularly preferred compounds contemplated for use in the present invention and first and second subsets of the general structural formula, respectively. With reference to the general structural formula of FIG. 1a, the X, Y, and Z moieties may be $CH_2$, NH, S, $SO_2$, CO, or O with the caveat that the X, Y, and Z moieties are each different from one another. In addition, $R_{2-6}$ are either hydrogen, halogen, a substituted or unsubstituted $C_{1-3}$ alkyl group (up to three carbons in length), or a $C_{1-3}$ ester or ether, and these moieties may be the same or different, or they may be alkyl moieties of aliphatic or aromatic rings incorporating two $R_{2-6}$ sites. The $R_{7-8}$ positions are hydrogen, halogen, methyl, ethyl, propyl, isopropyl, neopentyl, butyl, or substituted or unsubstituted aryl (phenyl, naphthyl, etc.) groups and these moieties may be the same or different, or they may be alkyl moieties as part of a substituted or unsubstituted aliphatic (e.g., cyclobutyl, cyclopentyl, or cyclohexyl) ring connecting $R_7$ and $R_8$. The $R_9$ position is a hydrogen, $C_{1-3}$ lower-alkyl such as methyl, ethyl or propyl, or a salt cation such as sodium, potassium, or ammonium, etc.

Figure 2A:
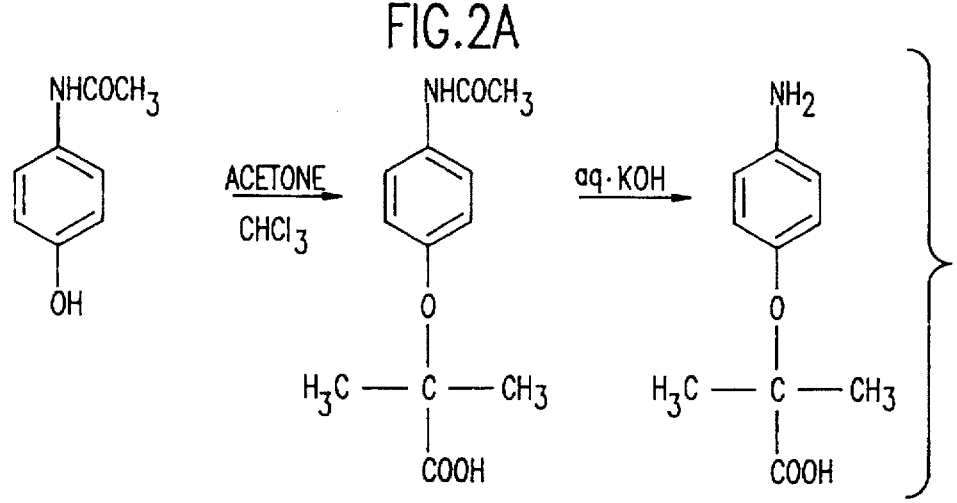
FIGS. 2a–b depict chemical structures of precursor compounds arranged in reaction schemes for preparing compounds that are useful as intermediates for synthesizing compounds within a first group of the family of compounds.
Figure 2B:
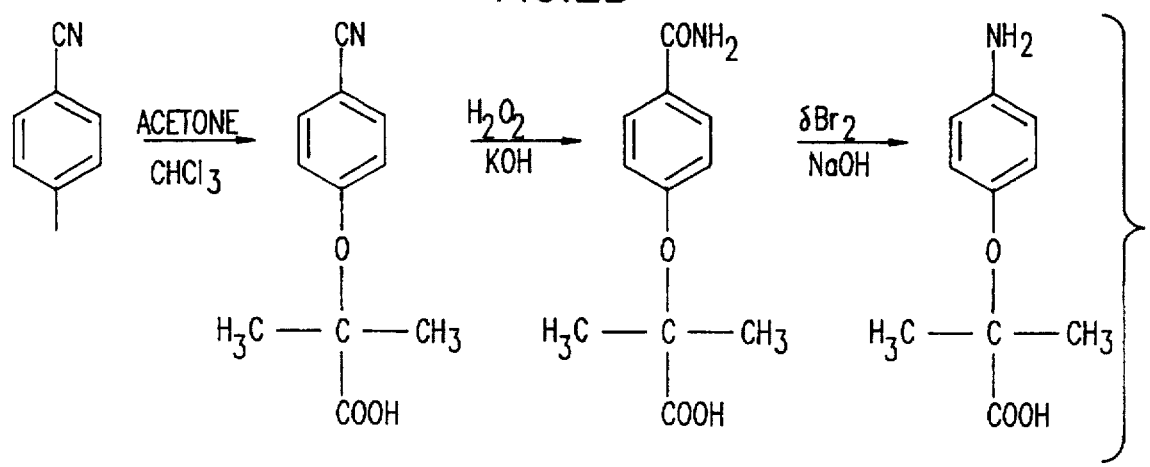
Figure 2C:
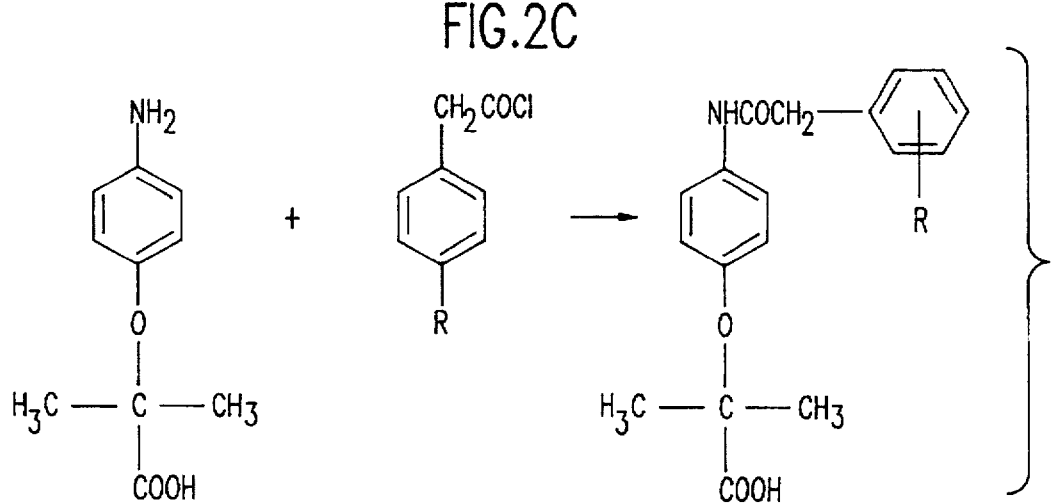
FIG. 2c depicts chemical structures, including the intermediates produced as shown in FIGS. 2a–b, arranged in a reaction scheme to prepare the first group of preferred compounds.
Figure 3:
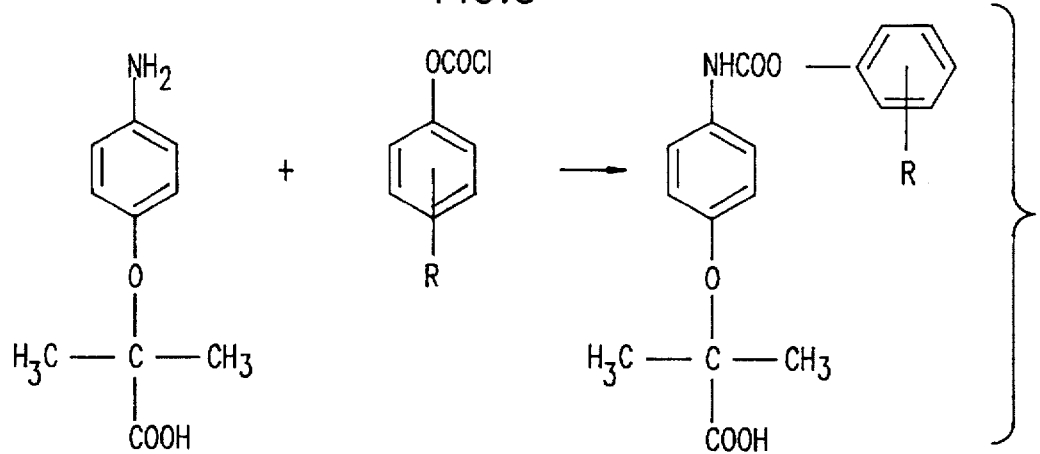
FIG. 3 depicts chemical structures arranged in a reaction scheme to produce a second group of the family of preferred compounds.
Figure 4:
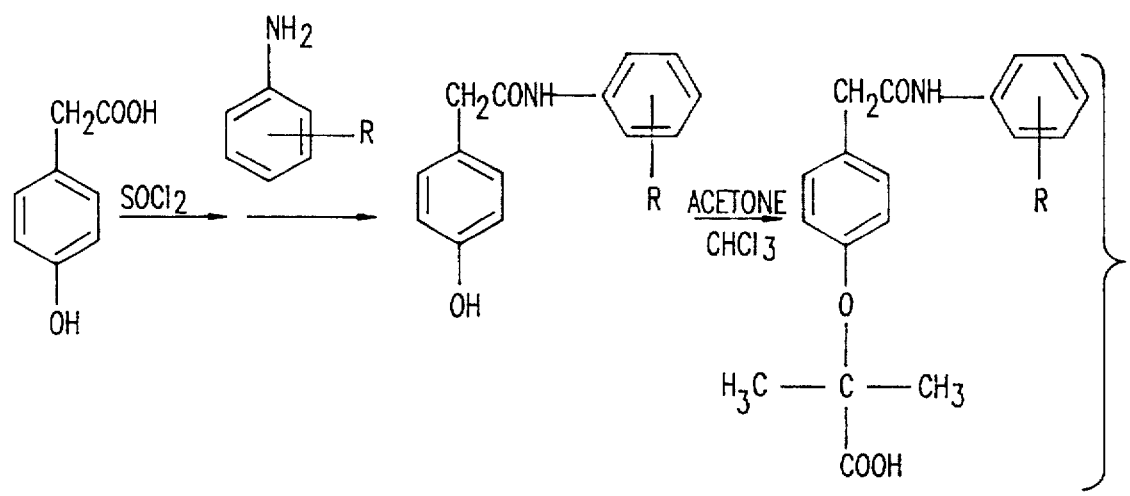
FIG. 4 depicts chemical structures arranged in a reaction scheme to produce a third group of the family of preferred compounds.
Figure 5A:
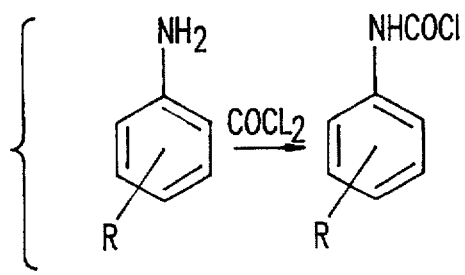
FIG. 5a–b depict chemical structures of precursor compounds arranged in reaction schemes for preparing compounds that are useful as intermediates for synthesizing compounds within a fourth group of the family of preferred compounds.
Figure 5B:
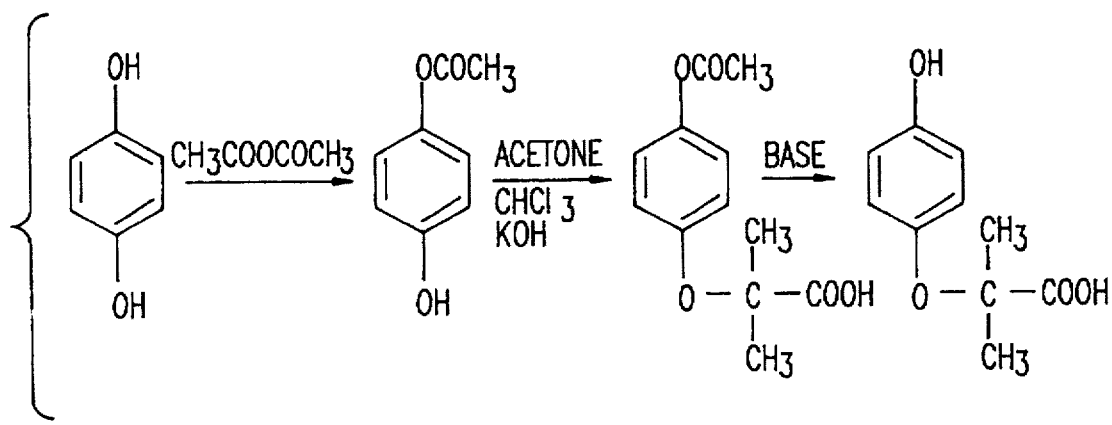
Figure 5C:
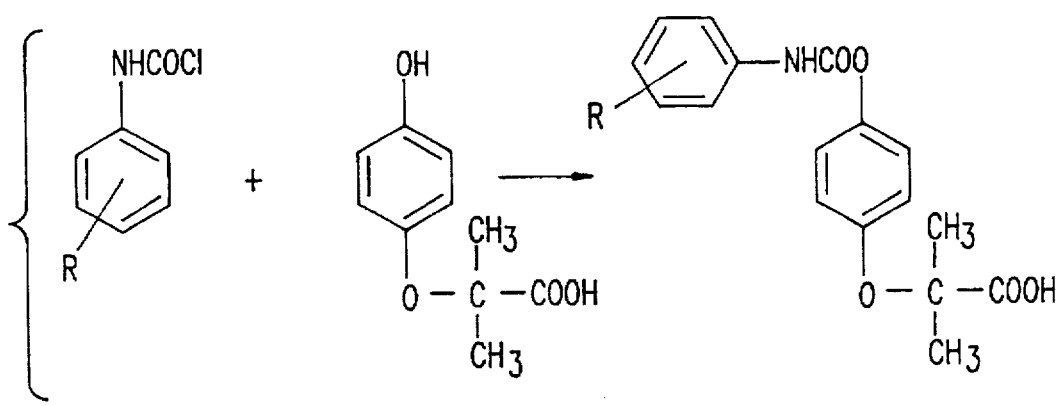
FIG. 5c depicts chemical structures, including the intermediates produced in FIGS. 5a–b, arranged in a reaction scheme to produce the fourth group of compounds.
Figure 6A:
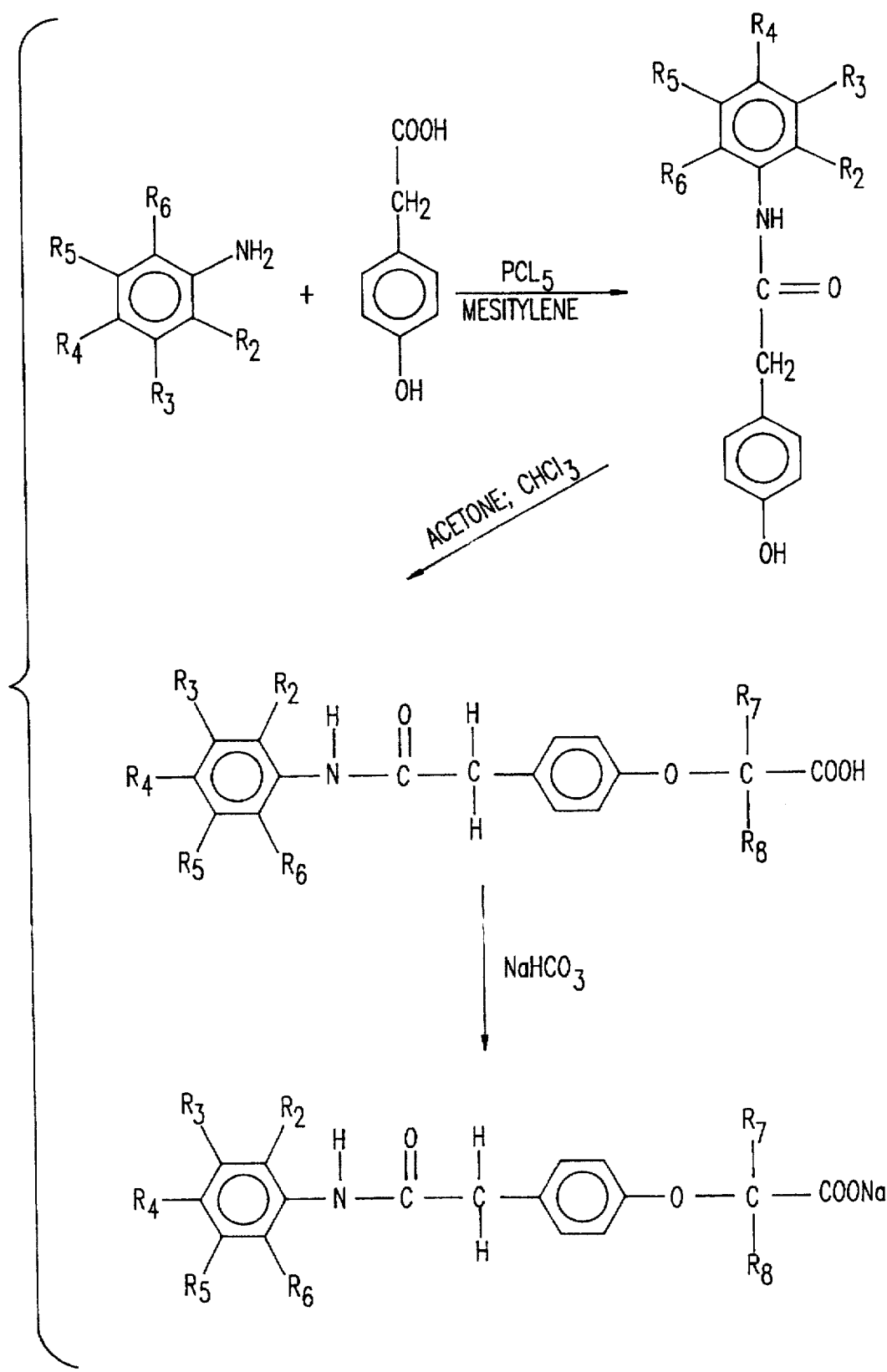
FIG. 6a depicts chemical structures arranged in a reaction scheme, which is an alternative to that shown in FIG. 4, for producing compounds within a third group of the family of preferred compounds.

In the first subset of compounds defined in FIG. 1b, X and Z may each be $CH_2$, NH, S, $SO_2$ or O, with the caveat that X and Z are different constituents. The first subset of compounds includes, in addition to others, the following four groupings:

Group I: 2-[4-((aryl)acetamido)phenoxy]-2-methyl propionic acid compounds having the general structural formula illustrated in FIG. 2C;

Group II: 2-[4-(((aryl)oxy)carbonyl)amino)phenoxy]-2-methyl propionic acid compounds having the general structural formula illustrated in FIG. 3;

Group III: 2-[4-((((aryl)amino)carbonyl)methyl)phenoxy]-2-methyl propionic acid compounds having the general structural formula illustrated in FIGS. 4 and 6a; and Group IV: 2-[4-(((aryl)amino)carbonyl)oxy)phenoxy]-2-methyl propionic acid compounds having the general structural formula illustrated in FIG. 5C.

Figure 7A:
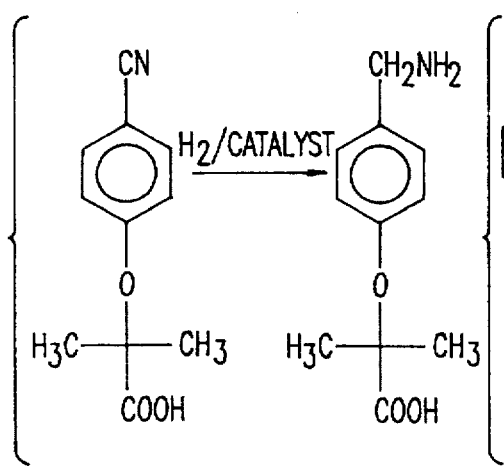
FIGS. 7a and 7b depict chemical structures arranged in a reaction scheme for producing compounds within a fifth group of the family of preferred compounds.
Figure 7B:
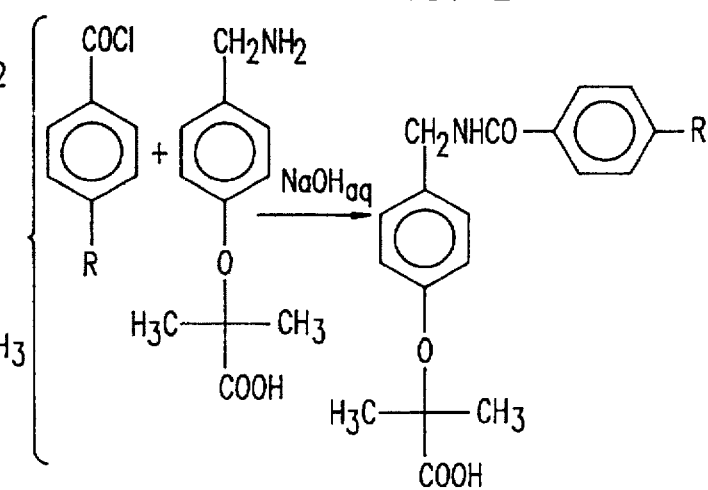

In the second subset of compounds defined in FIG. 1c, X and Z may each be CO, O, S, $SO_2$ or $CH_2$, with the caveat that when X and Z are different constituents. The second subset of compounds includes, in addition to other, the following two groupings:

Group V: 2-[4-(((aryloyl)amino)methyl)phenoxy]-2-methyl propionic acid compounds having the general structural formula illustrated in FIG. 7b.

Group VI: 2-[4-((((aryl)methyl)amino)carbonyl) phenoxy]-2-methylpropionic acid compounds which are the subject matter of the co-pending U.S. patent application Ser. No. 07/623,346 to Abraham et al. filed Dec. 7, 1990.

The $R_{2-9}$ substituents in FIGS. 1b–c are the same as those defined with reference to FIG. 1a. The synthesis of specific chemical compounds within the first five groups of compounds is provided in the following examples with reference to FIGS. 2–7. The synthesis of specific chemical compounds in the sixth group is explained in detail in co-pending U.S. patent application Ser. No. 07/623,346 to Abraham which is herein incorporated by reference. All compounds which were prepared were checked by thin layer chromatography (TLC) for purity and the structure elucidation was based on NMR and IR spectroscopy and elemental analysis.

EXAMPLE 1

FIG. 2A illustrates a reaction scheme for preparing 2-(4-aminophenoxy)-2-methyl propionic acid, a compound that is useful as a precursor in the preparation of Group I compounds. In accordance with the scheme of FIG. 2A, 8 grams (g) (0.2 mol) of pulverized sodium hydroxide is added to a suspension of 5.28 g (0.035 mol) of p-acetamidophenol in 23 ml (0.4 mol) of acetone. The reaction mixture is stirred at room temperature for ½ hour. Subsequently, 3.58 g (0.03 mol) of chloroform is added dropwise over the course of 30 minutes. The reaction mixture is stirred overnight at room temperature and acetone is removed under vacuum. The residue is dissolved in water (10 ml), followed by acidification with 37% hydrochloric acid (HCl) to produce a pale yellow precipitate of 2-(4-acetaminophenoxy)-2-methyl propionic acid (5 g, 60% yield), crystallized from methanol, mp 69°–71° C.

$^1$HNMR: (CD3OD) δ 7.1 (m,4H) Ar$\underline{H}$, 2.05 (s,3H), C$\underline{H}_3$, 1.45, (s,6H) 2C$\underline{H}_3$ 1.18 g (0.005 mol) of the 2-(4-acetaminophenoxy)-2-methyl propionic acid is boiled in 10% KOH (60 ml) for 1/2 hour. The solution is then cooled and acidified with acetic acid to yield 0.6 g (62% yield) of 2-(4-aminophenoxy)-2-methyl propionic acid as a yellowish white powder, mp 214°–16° C.

$^1$H NMR: (DMSOd6+TMS) δ 6.6 (m,4H)Ar$\underline{H}$, 1.35 (s,6H, 2C$\underline{H}_3$)

EXAMPLE 2

FIG. 2B illustrates another reaction scheme for preparing 2-(4-aminophenoxy)-2-methyl propionic acid. In accordance with the scheme of FIG. 2B, 8 grams of potassium hydroxide is dissolved in 32 ml of water and the resultant KOH solution is admixed with 280 ml of 3% hydrogen peroxide. 11.3 g (0.058 mol) of 2-(4-cyanophenoxy)-2-methyl propionic acid is slowly added to the KOH/$H_2O_2$ solution and the reaction mixture is stirred for about one hour until the exotherm and evolution of gas has ceased. The mixture is then cooled and acidified with concentrated hydrochloric acid. The 2-[4-(carboxamido)phenoxy]-2-methyl propionic acid product is obtained as a white solid (9.8 g, 79% yield). The product is crystallized from ethanol to produce pure white crystals, mp 202°–4° C.

5.57 g (0.025 mol) of the 2-[4-(carboxamido)phenoxy]-2-methyl propionic acid is added gradually with stirring to 100 ml of an ice cold aqueous solution containing 4.4 g (0.025 mol) of bromine and 11 g (0.25 mol) of sodium hydroxide. The solution thus obtained is warmed at 75° C. for ½ hour. After cooling, the solution is acidified with acetic acid giving the desired 2-(4-aminophenoxy)-2-methyl propionic acid product as 4.0 g (81% yield) of a white precipitate, mp 214°–16° C. The compound is identical with the product prepared in Example 1.

EXAMPLE 3

FIG. 2C illustrates a general reaction scheme for preparing the Group I 2-[4-(arylacetamido)phenoxy]-2-methyl propionic acids. In accordance with the illustrated scheme, 1 g (0.005 mol) of 2-(4-aminophenoxy)-2-methyl propionic acid is dissolved with stirring in 10 ml of water containing 0.41 g (0.1 mol) of NaOH. To this solution, 0.79 g (0.005 mol) of phenyl acetyl chloride in 5 ml of tetrahydrofuran (THF) is gradually added over a period of about 15 minutes. After the addition is complete the pH of the reaction mixture should be alkaline (if not a few drops of 2N NaOH is added to assure alkalinity). The reaction mixture is continuously stirred for 1 hour. Thereafter, the THF is evaporated in vacuo, and the solution is then diluted with 5 ml water and acidified with concentrated hydrochloric acid. The product is extracted with ethyl ether (2×20 ml), washed with water (3×20 ml), and then dried over anhydrous $MgSO_4$. Upon addition of petroleum ether to the ether solution, 0.9 g (56% yield) of the 2-[4-(phenylacetamido)phenoxy]-2-methyl propionic acid product precipitates as a pale brown solid, mp 173°–175° C.

$^1$H NMR: (DMSOd6) 10 (s,1H, COO$\underline{H}$), 7.5–6.7 (m, 9H, Ar$\underline{H}$), 3.55 (s, 2H, C$\underline{H}_2$), 1.4 (s, 6H, 2C$\underline{H}_3$) Anal: $C_{18}H_{19}NO_4$ Calculated C 69.00 H 6.07 N 4.47 Found C 68.86 H 6.14 N 4.42

EXAMPLE 4

The procedure of Example 3 is followed as above, except that 0.005 mol of 4-chlorophenyl acetyl chloride is substituted for the phenyl acetyl chloride. In this case the product (57% yield) is 2-[4-(p-chlorophenylacetamido)phenoxy]-2-methyl propionic acid, mp 168°–71° C.

$^1$H NMR: (DMSOd6) δ 10 (s, 1H, COO$\underline{H}$), 7.6–6.7 (m, 8H, Ar$\underline{H}$), 3.6 (s, 2H, C$\underline{H}_2$), 1.4 (s, 6H, 2C$\underline{H}_3$) Anal: $C_{18}H_{18}NO_4Cl$ Calculated C 62.15 H 5.17 N 4.02 Cl 10.12 Found C 62.16 H 5.25 N 3.98 Cl 10.25

The 4-chlorophenyl acetyl chloride for the foregoing synthesis is prepared by heating to reflux a suspension of 1 g (0.006 mol) of 4-chlorophenyl acetic acid in 1.07 g (0.009 mol) of thionyl chloride with stirring for 1 hour. After cooling, excess thionyl chloride is evaporated under vacuum to present the 4-chlorophenyl acetyl chloride product as a yellow oil (1 g, 83% yield).

EXAMPLE 5

FIG. 3 illustrates a general reaction scheme for preparing the Group II 2-[4-(((aryloxy)carbonyl) amino)phenoxy]-2-methyl propionic acids. In accordance with the illustrated scheme, a solution consisting of 0.15 g (0.001 mol) of phenyl chloroformate in 3 ml THF is gradually added to an ice cold solution containing 0.3 g (0.001 mol) of 2-(4-amino phenoxy)-2-methyl propionic acid and 0.17 g (0.002 mol) of sodium bicarbonate in 10 ml of water (10 ml). The reaction mixture is stirred for ½ hour at 0° C., followed by stirring for 1 hour at room temperature. The THF is removed in vacuo and 10 ml of water is added. Then, the reaction mixture is acidified with concentrated hydrochloric acid and extracted with ethyl ether (2×20 ml). The ether solution is washed with water (3×20 ml) and dried over anhydrous $MgSO_4$. The desired product, 2-[4-((((phenyl)oxy)carbonyl)amino) phenoxy]-2-methyl propionic acid, is precipitated from the ether solution by addition of petroleum ether as a white solid, 0.15 g (31% yield), mp 183°–5° C.

$^1$H NMR: (DMSOd6) δ 10 (s. 1H, COO$\underline{H}$), 7.55–6.75 (m, 9H, Ar$\underline{H}$), 1.4 (s, 6H, 2C$\underline{H}_3$) Anal: $C_{17}H_{17}O_5N$ Calculated C 64.76 H 5.39 N 4.44 Found C 64.65 H 5.45 N 4.43

EXAMPLE 6

The procedure for Example 5 is followed as above except that 0.001 mol of 4-chlorophenyl chloroformate is substituted for the phenyl chloroformate. In this case the 2-[4-(( ((p-chlorophenyl)oxy)carbonyl)amino)phenoxy]-2-methyl propionic acid product is obtained as a white precipitate, 0.15 g (28% yield), mp 179°–82° C.

$^1$H NMR: (DMSOd$_6$+TMS) δ 7.6–6.8 (m, 8H, Ar$\underline{H}$), 1.4 (s, 6H, 2C$\underline{H}_3$) Anal: $C_{17}H_{16}O_5NCl$ Calculated C 58.36 H 4.57 Cl 10.15 Found C 58.16 H 4.68 Cl 10.35

EXAMPLE 7

FIG. 4 illustrates a general reaction scheme for preparing the Group III compounds of the invention. In accordance with the illustrated scheme, 5.2 g (34 mmol) of 4-hydroxyphenylacetic acid (HPAA) is heated to reflux with an excess of thionyl chloride ($SOCl_2$) for ½ hour. The reaction mixture is then cooled and excess $SOCl_2$ is removed under vacuum. The residue is reacted for 2 hours with 6.3 g (68 mmol) of aniline in 50 ml of refluxing xylene. The reaction mixture is then cooled, washed with dilute HCl, water and brine and extracted with aqueous 2N NaOH. The combined alkali layer is washed with ether, cooled and acidified to provide 7 g of solid N-phenyl-4-hydroxybenzyl amide ($C_{14}H_{12}NO_2$) as an intermediate product (90% yield), mp 138° C. The intermediate product is recrystallized from a 1:2 mixture of acetone and petroleum ether and a 1.13 g (5 mmol) portion is O-alkylated for 12 hours using the procedure of Example 1 with 20 ml acetone, 2.75 g NaOH and 1.25 ml $CHCl_3$. The final product is 2-[4-((((phenyl)amino)carbonyl)methyl)phenoxy]-2-methyl propionic acid ($C_{18}H_{19}NO_4$), 1.2 g (76% yield), mp 198° C.

EXAMPLE 8

The procedure of Example 7 is repeated using 8.6 g (68 mmol) of 4-chloroaniline rather than the aniline. In this case, the intermediate product is N-(4-chlorophenyl)-4-hydroxy benzylamide ($C_{14}H_{12}ClNO_2$), 7.5 g (84% yield), mp 163° C. 1.3 g of the intermediate product is O-alkylated to produce 2-[4-((((4-chlorophenyl)amino)carbonyl)methyl) phenoxy]-2-methyl propionic acid ($C_{18}H_{18}ClNO_4$), 0.86 g (50% yield), mp 196° C.

EXAMPLE 9

The procedure of Example 7 is repeated using 2.6 g (17 mmol) of the HPAA and using 5.67 g (35 mmol) of 3,4- dichloroaniline rather than aniline. In this case, the intermediate product is N-(3,4-dichlorophenyl-4-hydroxy benzylamide ($C_{14}H_{11}Cl_2NO_2$). 1.48 g (5 mmol) of the intermediate is O-alkylated to produce 2-[4-(((3,4-dichlorophenyl)amino) carbonyl)methyl)phenoxy]-2-methyl propionic acid ($C_{18}H_{17}Cl_2NO_4$), 0.76 g (40% yield), mp 174° C.

EXAMPLE 10

The procedure of Example 7 is repeated using 2.6 (17 mmol) of the HPAA and using 5.7 g (35 mmol) of 3,5-dichloroaniline rather than aniline. In this case, the intermediate product is N-(3,5-dichlorophenyl-4-hydroxy benzylamide ($C_{14}H_{11}Cl_2NO_2$). 1.48 g (5 mmol) of the intermediate is O-alkylated to produce 2-[4-((((3,5-dichlorophenyl) amino)carbonyl)methyl)phenoxy]-2-methyl propionic acid ($C_{18}H_{17}Cl_2NO_4$), 0.8 g (42% yield), mp 138° C.

EXAMPLE 11

The procedure of Example 7 is repeated using 0.95 g (6 mmol) of the HPAA, 2.6 g (12 mmol) of 3,4,5-trichloroaniline rather than aniline, and 25 ml of refluxing xylene. In this case, the intermediate product is N-(3,4,5-trichlorophenyl)-4-hydroxy benzylamide. 0.50 g (1.5 mmol) of the intermediate product is O-alkylated using 10 ml acetone, 0.82 g NaOH and 0.37 ml CHCl$_3$ to produce 2-[4-((((3,4,5-trichlorophenyl)amino)carbonyl)methyl) phenoxy]-2-methyl propionic acid ($C_{18}H_{16}Cl_3NO_4$), 0.27 g (43% yield), mp 160° C.

EXAMPLE 12

The procedure of Example 7 is repeated using 5.04 g (32 mmol) of the HPAA, 6 ml (64 mmol) of 4-fluoroaniline rather than aniline, and 25 ml of refluxing xylene. In this case, the intermediate product is N-(4-fluorophenyl)-4-hydroxybenzylamide. 1.22 g (5 mmol) of the intermediate product is O-alkylated to produce 2-[4-((((4-fluorophenyl) amino)carbonyl)methyl)phenoxy]-2-methyl propionic acid ($C_{18}H_{18}FNO_4$), 0.74 g (45% yield), mp 198° C.

EXAMPLE 13

The procedure of Example 7 is repeated using 5.04 (32 mmol) of the HPAA, 8.05 ml (64 mmol) of 4-trifluoromethylaniline rather than aniline, and 25 ml of refluxing xylene. In this case, the intermediate product is N-(4-trifluoromethylphenyl)-4-hydroxy benzylamide. 1.5 g (5 mmol) of the intermediate is used to produce 2-[4-((((4-trifluoromethylphenyl)amino)carbonyl)methyl)phenoxy]-2-methyl propionic acid ($C_{19}H_{18}F_3NO_4$), 0.85 g (44% yield), mp 197° C.

EXAMPLE 14

The procedure of Example 7 is repeated using 5.04 (32 mmol) of the HPAA, 8 g (65 mmol) of 4-methyl aniline rather than aniline, and using 25 ml of refluxing xylene. In this case the intermediate product is N-(4-methylphenyl)-4-hydroxy benzylamide. 1.2 g (5 mmol) of the intermediate is used to produce 2-[4-((((4-methylphenyl)amino)carbonyl) methyl)phenoxy]-2-methyl propionic acid ($C_{19}H_{21}NO_4$), 0.98 g (65% yield), mp 164° C.

EXAMPLE 15

The procedure of Example 7 is repeated using 3.26 (21 mmol) of the HPAA, 5.3 ml (42 mmol) of 3,5-dimethyl aniline rather than aniline, and 25 ml of refluxing xylene. In this case the intermediate product is N-(3,5-dimethylphenyl)-4-hydroxy benzylamide. 1.27 g (5 mmol) of the intermediate is used to produce 2-[4-((((3,5-dimethylphenyl)amino) carbonyl)methyl)phenoxy]-2-methyl propionic acid ($C_{20}H_{23}NO_4$), 1.15 g (68% yield), mp 85° C. Alternatively, the procedure outlined in the German Patent Application 2,432,560, which is herein incorporated by reference, can be followed to produce the compound of this Example 15.

EXAMPLE 16

The procedure of Example 7 is repeated using 5.04 (32 mmol) of the HPAA, 10 ml (64 mmol) of 4-isopropyl aniline rather than aniline, and using 25 ml of refluxing xylene. In this case the intermediate product is N-(4-isopropylphenyl) -4-hydroxybenzylamide. 1.34 g (5 mmol) of the semi-solid, thick viscous liquid intermediate is used to prepare 2-[4-(( ((4-isopropylphenyl)amino)carbonyl)methyl)phenoxy]-2-methyl propionic acid ($C_{21}H_{25}NO_4$), 1.1 g (61% yield), mp 141° C.

EXAMPLE 17

With reference to FIGS. 5A, 5B and 5C, a scheme is illustrated for preparing Group IV compounds. In accordance with FIG. 5A, aniline or aniline derivatives may be reacted with phosgene to obtain the carbamoyl chloride. In accordance with FIG. 5B, hydroquinone may be monoacetylated using acetic anhydride. The product is then O-alkylated using acetone, CHCl$_3$ and KOH and then hydrolyzed using a base. The products of the reactions of FIGS. 5A and 5B may then be reacted according to the reaction scheme of FIG. 5C to produce the Group IV 2-[4-(((arylamino) carbonyl)oxy)phenoxy)]-2-methyl propionic acids.

EXAMPLE 18

As an alternative to the reaction scheme described in Example 7 and shown in FIG. 4, the Group III compounds may be prepared according to the scheme shown in FIG. 6a. 5.2 g (32 mmol) of HPAA, 6.3 g (68 mmol) of aniline, and 25 ml of mesitylene are heated to reflux. 0.74 g (8mmol) of phosphorous pentachloride is added to the refluxing mixture and the reflux is continued for an additional two hours. The reaction mixture is subsequently cooled, washed with dilute HCl, water and brine, and extracted with aqueous 2N sodium hydroxide NaOH. The combined alkali layer is washed with ether, cooled and acidified to provide 7 g (90% yield) of solid N-phenyl-4-hydroxybenzyl amide ($C_{14}H_{12}NO_2$) as an intermediate product, mp 138° . The intermediate product is recrystallized from a 1:2 mixture of acetone:petroleum ether and a 1.13 g (5 mmol) portion is O-alkylated. 1.6 g (30 mmol) of pulverized sodium hydroxide is added to a solution of N-phenyl-4-hydroxybenzamide (1.13 g, 5 mmol) in 20 ml of acetone. The reaction mixture is stirred overnight at room temperature and acetone is removed under vacuum. The residue is dissolved in 10 ml of water and acidified with 2N HCl to produce a pale yellow solid. The solid is separated, dissolved in methanol, charcoalated, and solvent evaporated to provide 2-[4-((( (phenyl)amino)carbonyl)methyl)phenoxy]-2-methyl propionic acid ($C_{18}H_{19}NO_4$), 1.2 g (76% yield), mp 198° C. The last step in the procedure shown in FIG. 6a is the conversion of the acid to the sodium salt via its reaction with sodium bicarbonate. Similar reactions with other salt cations such as potassium and ammonium or reactions to form esters (e.g., methyl, ethyl, propyl, etc.) can also be performed.

EXAMPLE 19a

Figure 6B:
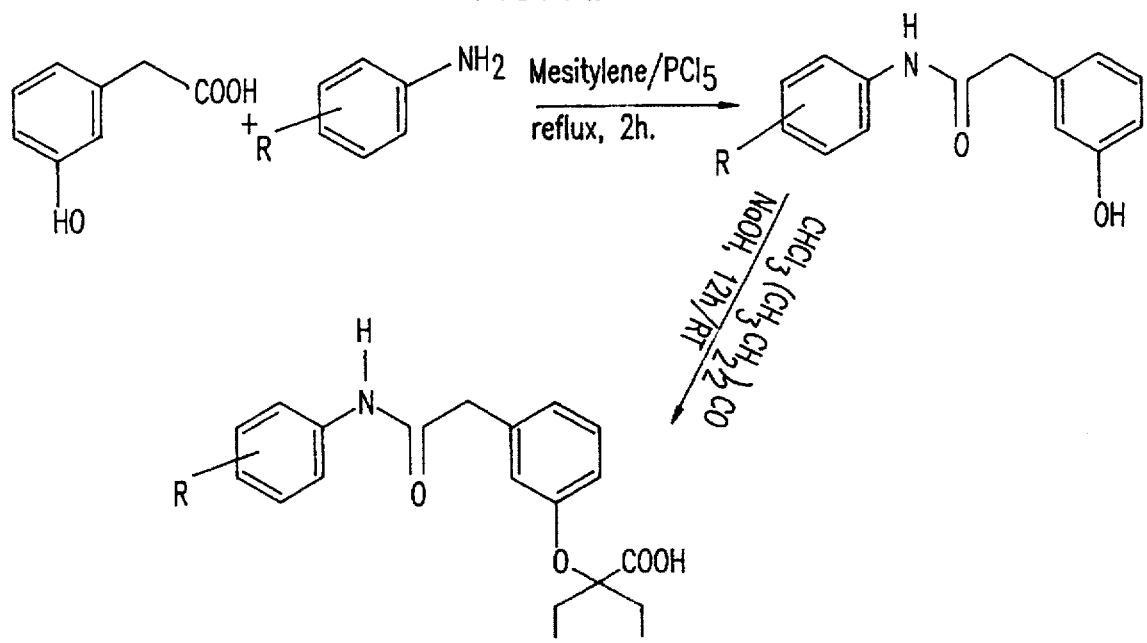
FIG. 6b depicts chemical structures arranged in a reaction scheme similar to that shown in FIG. 6a, except that the precursor compounds utilized are chosen such that the compound produced has a meta-substitution rather than para-substitution on one phenyl ring and so that ethyl rather than methyl groups are present on the substituent moiety of the meta-substituted phenyl ring.

FIG. 6b presents a similar reaction scheme to FIG. 6a, except that 3- rather than 4-hydroxyphenylacetic acid (HPAA) is used as the precursor material so that the final compound has a meta rather than a para substitution. In addition, rather than reacting with acetone (dimethyl ketone) a diethyl ketone is used to position ethyl, rather than methyl, moieties in the group substituted on one of the phenyl rings. By example, 1.5g (10mmol) 3-HPAA and 2.6g (20 mmol) 4-chloroaniline in 20 ml of mesitylene was heated to reflux. Then 0.33 g (2.55 mmol) PCl$_5$ was then slowly added to the above refluxing solution and the refluxing was continued for two hours. The reaction mixture was then cooled and then worked up as described above to yield 2.2 g (90% yield) of 3-[((4-chloroanilino) carbonyl)methyl]phenol. As described above, chloroform (0.8 ml) was added to a stirred and ice-cooled mixture of 1.23 grams of 3-[((4-chloroanilino) carbonyl)methyl]phenol and 1.6 g NaOH in 15 ml of acetone. The reaction mixture was allowed to warm to room temperature and stirring continued for an additional 10 hours. The usual work-up yielded 2-[3-(((4-chloroanalino) carbonyl)methyl)]phenoxy]-2-methylpropionic acid as a low temperature melting sticky solid (C,H,Cl,N analysis yielded (C$_{18}$H$_{18}$ClNO$_4$); NMR δPPM: 1.42 (6H, s, CH$_3$), 3.61 (2H, s, benzylic CH$_2$), and 6.6–7.75 (8H, m, aromatic H)). However, rather than using acetone as the reaction solvent, diethylketone can be used in the same manner as described above to yield the butanoic acid (as opposed to propanoic acid) structure shown in FIG. 6b.

EXAMPLE 19b

Figure 6C:
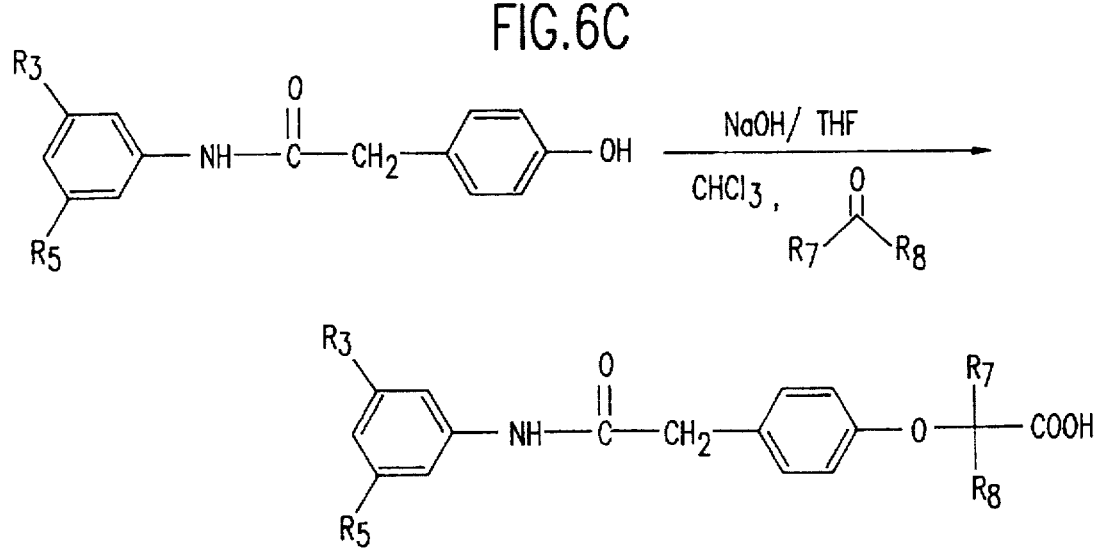
FIG. 6c depicts chemical structures arranged in a reaction scheme whereby groups larger than ethyl are introduced into the acid moiety of compounds of Group III.

FIG. 6c describes a general reaction scheme to introduce groups larger than methyl on the acid moiety of compounds of Group III.

N-(3,5-dimethylphenyl)-4-hydroxyphenylacetamide (3.06 gms, 12 mmol) in THF is treated with 2.4 gms (60 mmol) of NaOH at −20° C. 5.45 ml (60 mmol) of isobutyraldehyde and 4.8 ml (60 mmol) of CHCl$_3$ is added dropwise simultaneously at −20° C. and stirring continued overnight at room temperature. THF is removed under vacuum and the residue is dissolved in water, followed by acidification with 35% HCl. The precipitated solid is extracted into ether and treated with 6% NaHCO$_3$ solution. The aqueous layer on acidification yields the product 3-methyl-2-[4-((((3,5-dimethylphenyl)amino)carbonyl)methyl)phenoxy]butanoic acid (C$_{21}$H$_{25}$NO$_4$) (yield 1 gm, 23.5%) mp (uncorrected) 96°–100° C.

NMR: acetone-d$_6$ 1.1 (6H, d, 2 CH$_3$ of isopropyl), 1.3 (1H, m, C$_H$ of isopropyl), 6.7–7.3 (7H, m, ArH)

EXAMPLE 19c

The procedure of Example 19b is repeated using 0.507 gms (2 mmol) of N-(3,5-dimethylphenyl)-4-hydroxyphenyl acetamide, 0.8 gms (20 mmol) of NaOH, 1.6 ml (20 mmol) of CHCl$_3$ and 2 ml (20 mmol) of 3,3-dimethylphenyl) amino)carbonyl)methyl)phenoxy]pentanoic acid (C$_{23}$H$_{29}$NO$_4$) (yield 0.310 gms, 40.6%) mp (uncorrected) 118°–125° C.

NMR: acetone-d$_6$, 1.0 (9H, s, CH$_3$), 1.8 (m, CH$_2$), 2.2 (6H, s, 2ArCH$_3$), 3.6 (2H, s, CH$_2$ adjacent to carbonyl), 4.6 (1H, dd, CH), 6.7–7.3 (7H, m, ArH).

EXAMPLE 20

With reference to FIGS. 7a, a general reaction scheme for preparing 2-[4-(aminomethyl)phenoxy]-2-methyl propionic acid, a compound that is useful as a precursor to the preparation of the Group V compounds, is presented. In accordance with the illustrated scheme, 2-[4-cyanophenoxy] -2-methyl propionic acid (2g, 9mmol), prepared as described in Example 2, and 75 ml of ethanol were placed in a 250 ml Parr hydrogenation bottle. The solution was acidified with concentrated hydrochloric acid (3 ml), then 10% palladium on activated charcoal (0.2 g, 10% wt) was added to the mixture. The reaction mixture was placed on a Parr hydrogenator apparatus at 45 psi of hydrogen pressure and shaken for a period of two hours. The mixture was filtered to remove the catalyst, and the filtrate concentrated under vacuum. Addition of ether precipitated hydrochloride salt of the desired product as white, shiny crystals (2.1 g, 87%).

EXAMPLE 21

FIG. 7B illustrates a general reaction scheme for preparing the Group V compounds used in the present invention. In accordance with the illustration, a solution of benzoyl chloride (0.14 g, 1 mmol) in THF (3 ml) was added over a 15 minute period to a stirred solution of 2-[4-(aminomethyl) phenoxy]-2-methylpropionic acid (0.24 g, 1 mmol) and NaOH (0.08 g, 2 mmol) in 10 ml of water. After the addition of the benzoyl chloride was completed, the reaction mixture was stirred for 1 hour at room temperature. THF was evaporated in vacuo. Acidification of the residue provided the desired compound as an oil which was extracted with ether. The organic layer was washed with water, brine, and aired over anhydrous MgSO$_4$. Subsequent addition of petroleum ether precipitated 2-[4-(benzoylamino)methyl) phenoxy]-2-methyl propionic acid (C$_{18}$H$_{19}$NO$_4$) as a white solid (0.15 g, 48%) mp 176°–179° C.

NMR: (DMSO-d$_6$) δ 1.45 (6H, s, 2CH$_3$), 4.4 (2H, d, CH$_2$), 6.8–7.2 (4H, dd, J=9 Hz, aromatic H, 7.4–8 (5 H, m, aromatic H), 9, (1 H, br t, NH).

EXAMPLE 22

The procedure of Example 21 is repeated using 2-chlorobenzoyl chloride (1 mmol) rather than benzoyl chloride. In this case, the product (58% yield) is 2[4-(((2-chlorobenzoyl)amino)methyl)phenoxy]-2-methyl propionic acid (C$_{18}$H$_{18}$ClNO$_4$) mp 135°–137° C.

EXAMPLE 23

The procedure of Example 21 is repeated, except that 1 mmol of 3-chlorobenzoyl chloride is substituted for benzoyl chloride. In this case, the product (53% yield) is 2-[4-(((3-chlorobenzoyl)amino)methyl)phenoxy]-2-methyl propionic acid (C$_{18}$H$_{18}$ClNO$_4$) mp 145°–146° C.

EXAMPLE 24

The procedure of Example 21 is repeated, except that 1 mmol of 4-chlorobenzoyl chloride is substituted for benzoyl chloride. In this case, the product (63% yield) is 2-[4-(((4-chlorobenzoyl)amino)methyl)phenoxy]-2-methyl propionic acid (C$_{18}$H$_{18}$ClNO$_4$) mp 186°–189° C.

EXAMPLE 25

The procedure of Example 21 is repeated, except that 1 mmol of 3,4-dichlorobenzoyl chloride is substituted for benzoyl chloride. In this case, the product (57% yield) is 2-[4-(((3,4-dichlorobenzoyl)amino)methyl)phenoxy]-2-methyl propionic acid (C$_{18}$H$_{17}$Cl$_2$NO$_4$) mp 186°–189° C.

EXAMPLE 26

The procedure of Example 20 is repeated, except that 1 mmol of 3,5-dichlorobenzoyl chloride is substituted for benzoyl chloride. In this case, the product (43% yield) is 2-[4-(((3,5-dichlorobenzoyl)amino)methyl)phenoxy]-2-methyl propionic acid ($C_{18}H_{17}Cl_2NO_4$) mp 110°–113° C.

EXAMPLE 27

The procedure of Example 20 is repeated, except that 1 mmol of 3,4,5-trichlorobenzoyl chloride is substituted for benzoyl chloride. In this case, the product is 2-[4-(((3,4,5-trichlorobenzoyl)amino)methyl)phenoxy]-2-methyl propionic acid ($C_{18}H_{16}Cl_3NO_4$) mp 151°–152° C.

EXAMPLE 28

The procedure of Example 21 is repeated, except that 1 mmol of p-toluene sulphonyl chloride is substituted for benzoyl chloride. In this case, the product is 2-[(4-methyl phenyl)sulfonamide methyl)phenoxy-2-methyl propionic acid ($C_{18}H_{21}NSO_5$) mp 108° C.

EXAMPLE 29

N-(3,5-dimethylphenyl)-4-hydroxyphenylacetamide (3.06 gms, 12 mmol) in THF is treated with 2.4 gms (60 mmol) of NaOH at −20° C. Subsequently 5.889 gms (60 mmol) of cyclohexanone and 4.8 ml (60 mmol) of $CHCl_3$ is added dropwise simultaneously at −20° C. and stirred overnight at room temperature. THF is removed under vacuum and the residue is dissolved in water, followed by acidification with 35% HCl. The precipitated solid is extracted into ether and treated with 6% sodium bicarbonate solution. The aqueous layer on acidification with HCl yields the product 1-[4-(((3,5-dimethylphenyl)amino)carbonyl)methyl) phenoxy]cyclohexanecarboxylic acid ($C_{23}H_{27}NO_4$). The product was purified by repeated extraction into ether and $NaHCO_3$.

NMR: (acetone-$d_6$) 2.2 (6H, s, $2CH_3$), 3.6 (2H, s, $CH_2$), 1.5–2 (brm, cyclohexyl ring protons), 6.7–7.2 (7H, m, Ar H).

EXAMPLE 30

The procedure of Example 29 is repeated with 1.02 gms (4 mmol) of N-(3,5-dimethylphenyl)-4-hydroxyphenyl acetamide, 0.8 gms (20 mmol) of NaOH, 1.6 mL (20 mmol) of $CHCl_3$ and 1.77 mL (20 mmol) of cyclopentanone to prepare 1-[4-((((3,5-dimethylphenyl)amino)carbonyl) methyl) phenoxy]cyclopentane carboxylic acid ($C_{22}H_{25}NO_4$) (yield 0.100 gms, 6.8%) mp (uncorrected) 88°–94° C.

NMR: (acetone-$d_6$) 1.8–2.3 (brm, cyclopentyl ring protons), 2.2 (6H, s, 2 $CH_3$), 3.56 (2H, s, $CH_2$), 6.7–7.3 (7H, m, ArH)

EXAMPLE 31

The procedure of Example 29 is repeated with 1.5 gms (5 mmol) of N-(3,5-dichlorophenyl)-4-hydroxyphenyl acetamide, 1 gm (25 mmol) of NaOH, 2 ml (25 mmol) of $CHCl_3$ and 1.17 gms (12 mmol) of cyclohexanone to prepare 1-[4-((((3,5-dichlorophenyl)amino)carbonyl)methyl) phenoxy]cyclohexanecarboxylic acid ($C_{20}H_{19}NO_4Cl_2$) (yield 0.22 gms, 10.3%) mp (uncorrected) 80°–90° C.

NMR: (acetone-$d_6$) 1.5–2 (10H, brm, cyclohexyl ring protons), 3.6 (2H, s, $CH_2$), 6.8–7.8 (7H, m, ArH).

EXAMPLE 32

The procedure of Example 30 is repeated using N-(3,5-dichlorophenyl)-4-hydroxyphenylacetamide and cyclopentanone to prepare 1-[4-((((3,5-dichlorophenyl)amino) carbonyl)methyl)phenoxy]cyclopentanecarboxylic acid ($C_{19}H_{17}NO_4Cl_2$).

Examples 1 through 32 outline the synthesis procedures for producing several compounds within the family of compounds defined by the general structural formula of FIG. 1a. Specifically, Examples 1–19 disclose synthesis procedures for Groups 1–4 compounds within the subset defined by the structural formula of FIG. 1b and Examples 20–27 disclose synthesis procedures for Group 5 compounds within the subset defined by the structural formula of FIG. 1c. The co-pending U.S. patent application Ser. No. 07/623, 346 to Abraham et al. filed Dec. 7, 1990, describes the synthesis procedures for Group 6 compounds within the subset defined by the structural formula of FIG. 1c. Example 28 provides synthesis procedures where a sulfur or sulfur dioxide is present at the X, Y, or Z positions with respect to FIG. 1a. Examples 29–32 provide synthesis procedures where a five or six membered aliphatic ring is connected to the propionic acid tail portion of the FIG. 1a molecule. It should be understood that many other compounds within the family of compounds used in the present invention can easily be synthesized by changing the starting materials. All compounds within the family would have a similar mode of binding and would, therefore, all should have the effect of shifting the allosteric equilibrium of hemoglobin towards favoring the low affinity "T" state.

One broad family of compounds contemplated for use in this invention includes compounds defined by the formula:

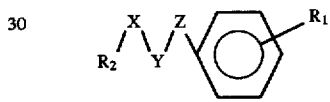

where $R_2$ is a substituted or unsubstituted aromatic such as a phenyl, naphthyl, or indanyl, or hetrocyclic aromatic, or a substituted or unsubstituted alkyl ring compound, such as a cyclohexyl or adamantyl, or a substituted or unsubstituted phthalimide compound that incorporates X and Y where X is a carbonyl, Y is a nitrogen and $R_2$ completes the phthalimide compound by being bonded to both X and Y, and, if $R_2$ is not a phthalamide compound, where X, Y, and Z are $CH_2$, NH, S, $SO_2$, CO or O with the caveat that the X, Y, and Z moieties are each different from one another, and where $R_1$ has the formula:

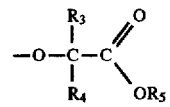

where R1 can be connected to any position on the phenyl ring and $R_3$ and $R_4$ are hydrogen, halogen, methyl, ethyl, propyl, isopropyl, neopentyl, butyl, or substituted or unsubstituted aryl (phenyl, naphthyl, etc.) groups and these moieties may be the same or different, or alkyl moieties as part of an aliphatic ring connecting $R_3$ and $R_4$, such as substituted 3, 4, 5, and 6 carbon atom rings, and $R_5$ is a hydrogen, $C_{1-3}$ loweralkyl such as methyl, ethyl or propyl, or a salt cation such as sodium, potassium, or ammonium. To this end, compounds having a naphthyl, adamantyl, or indanyl group at $R_1$ instead of the substituted phenyl like that shown in FIG. 1a have been prepared using substantially the same synthetic routes as described above. In addition, compounds having a phthalimide-like structure have also been synthesized as shown in FIGS. 12a–b and described below in EXAMPLE 33.

EXAMPLE 33

Figure 12A:
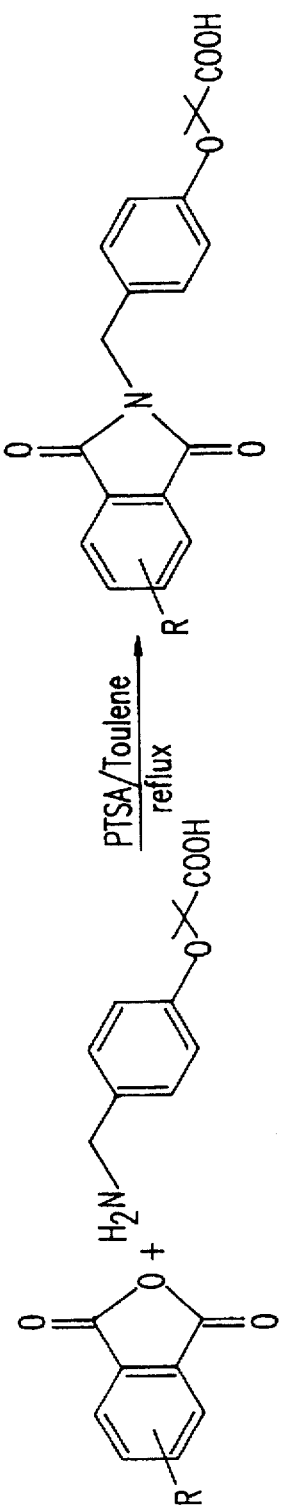
FIGS. 12a–b depict chemical structures in a reaction scheme used to produce a phthalimide form of the compounds within the present invention where the compounds were shown by a measured $P_{50}$ value to allosterically modify hemoglobin towards the low oxygen affinity state.
Figure 12B:
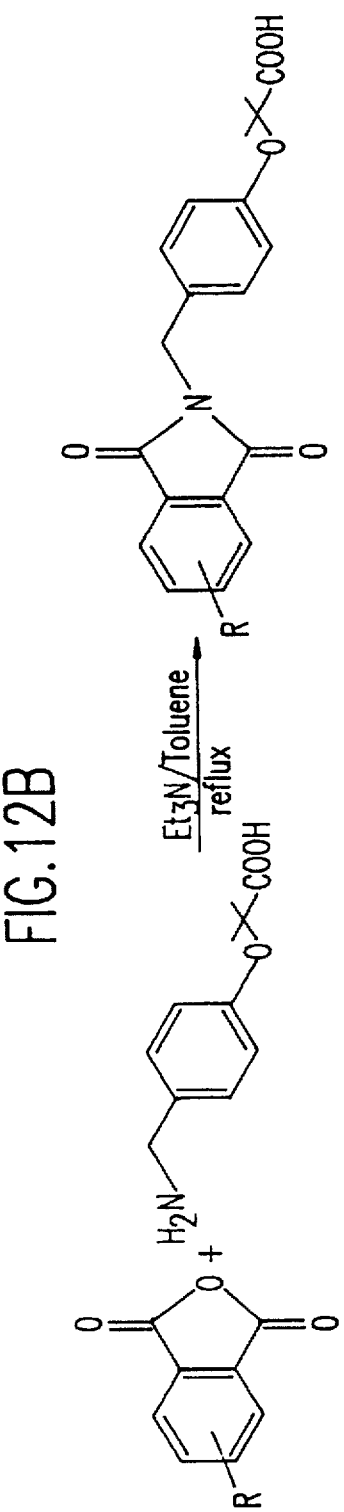

FIGS. 12a and 12b show alternative synthesis routes for preparing 2-[4-((phthalamido)N-methyl)phenoxy)-2-methyl proprionic acid. Phthalic anhydride (0.75 g; 5 mmol) and 2[4-((amino)methyl) phenoxy]-2-methyl proprionic acid (see FIG. 2B) were refluxed in 25 ml of toluene in the presence of 1 ml triethylamine. Water was removed azeotropically. After four hours of refluxing, the reaction mixture was cooled, toluene was separated, and the above-described work up was provide to yield a crystalline white residue (90% yield; mp 149° C.; NMR δ ppm: 1.46(6H, s, $CH_2$), 4.65(2H, s, $CH_2$), 6.75 and 7.2 (4H, d, J=6 Hz, aromatic H of a parasubstituted ring), and 7.85 (4H, s, aromatic H of a phthalimide unit).

To test the compounds of the invention for physiological activity, human blood was obtained from the Central Blood Bank, Richmond, Va. The extraction, chromatography, and characterization of isolated hemoglobin methods used by the inventors were identical to those described by Dozy and Huisman in *J. of Chromatography*, Vol 32, (1968) pp. 723 and in *The Chromatography of Hemoglobin*, H. J. Schroeder and D. H. J. Huisman, Ed. Marcel Dekker Inc. N.Y. (1980) which are herein incorporated by reference. The purity of normal hemoglobin (HbA) was determined by gel electrophoresis, using a Gelman semimicroelectrophoresis chamber. The concentration of hemoglobin was determined according to the cyanmethemoglobin method described in Zijlstra, *Clin. Chem. Acta.*, Vol 5, pp. 719–726 (1960), and Zijlstra and Van Kamper, *J. Clin. Chem. Clin. Biochem.*, Vol. 19, p. 521 (1981) which are herein incorporated by reference. All purified hemoglobin solutions were stored in liquid nitrogen. The reagents and buffers were purchased from the following sources: Fischer Scientific, Sigma Chemical Company, and Pharmacia and Research Chemicals, Inc.

Oxygen equilibrium curves were determined on an AMINCO™ HEM—O—SCAN oxygen dissociation analyzer available from Travenol Laboratories. HbA was prepared as follows: 20 ml of whole blood from a nonsmoking donor (blood bank. Richmond, Va.) was drawn into a heparinized vacutainer. The blood was immediately packed in ice (to prevent MetHb formation) and then centrifuged (10 minutes at 2500 rpm) to separate the plasma and buffy coat from the packed erythrocytes. After centrifugation was completed, the plasma and buffy coat were removed by aspiration and the cells washed three times with 0.9% NaCl containing 40 mg of ethylenediamine-tetraacetic acid (EDTA) per liter and then once with 1.0% NaCl containing 40 mg of EDTA/L. The cells were lysed by the addition of one to two volumes of deionized water containing 40 mg of EDTA/L. The mixture was allowed to stand for 30 minutes with occasional mixing before being centrifuged for two hours at 10,000 rpms at 4° C. for two hours to remove the remaining cell stroma. The supernatant was further purified by either gel filtration with Sephadex G-25 or dialysis against pH 8.6 tris buffer (50 mM, containing 40 mg. of EDTA/L). The sodium chloride free hemoglobin solution was chromatographed on DEAE-Sephacel ion-exchange resin (Sigma) preequilibrated with Tris buffer (pH 8.6, 50 mM, containing 40 mg of EDTA/L), the HbA fraction was then eluted with pH 8.4 Tris buffer. The pure HbA fraction (identified by electrophoresis) was concentrated using a Schleicher and Schuell collodion bag apparatus (Schleicher and Schuell, Inc.) with HEPES buffer (150 mM, pH 7.4) as the exchange buffer. The hemoglobin concentration was then determined using the above-noted cyanomethemoglobin method. The hemoglobin concentration at this point was usually found to be around 35 g% or approximately 5.5 mM. Less than 5% methemoglobin was noted even after several days at 4° C.

All compounds were mixed with one equivalent of sodium bicarbonate ($NaHCO_3$) (this process converts the carboxylic acid moiety to a sodium salt; see FIG. 6a; it is noted that other salts can be formed by similar process), then dissolved in the HEPES buffer to give 20 mM solutions. Just prior to running the oxygen equilibrium curve, the hemoglobin and the drug were mixed in a 1:1 ratio (50 µl of hemoglobin plus 50 µl of drug) to give 2.75 mM hemoglobin with a drug concentration of 10 mM. The control was prepared by the addition of 50 µl of hemoglobin to 50 µl of the HEPES buffer.

Table 1 presents the measured $P_{50}$ value, the $P_{50}$ control value, and the ratio of the measured $P_{50}$ value to the control ($P_{50}/P_{50}c$) for normal hemoglobin treated with several synthesized compounds. Note that the X, Y, Z and $R_2$–$R_8$ positions relate to FIG. 1a.

TABLE 1

| $R_2$ | $R_3$ | $R_4$ | $R_5$ | $R_6$ | X | Y | Z | $R_7$ | $R_8$ | $P_{50}c$ | $P_{50}$ | $P_{50}/P_{50}c$ |
|---|---|---|---|---|---|---|---|---|---|---|---|---|
| H | H | H | H | H | CO | NH | $CH_2$ | $CH_3$ | $CH_3$ | 18 | 35 | 1.94 |
| Cl | H | H | H | H | CO | NH | $CH_2$ | $CH_3$ | $CH_3$ | 18 | 27.5 | 1.52 |
| H | Cl | H | H | H | CO | NH | $CH_2$ | $CH_3$ | $CH_3$ | 18 | 37.5 | 2.08 |
| H | H | Cl | H | H | CO | NH | $CH_2$ | $CH_3$ | $CH_3$ | 19 | 48 | 2.52 |
| H | Cl | Cl | H | H | CO | NH | $CH_2$ | $CH_3$ | $CH_3$ | 18 | 40.5 | 2.25 |
| H | Cl | H | Cl | H | CO | NH | $CH_2$ | $CH_3$ | $CH_3$ | 18 | 47 | 2.6 |
| H | Cl | Cl | Cl | H | CO | NH | $CH_2$ | $CH_3$ | $CH_3$ | 19 | 40 | 2.1 |
| H | H | H | H | H | $CH_2$ | CO | NH | $CH_3$ | $CH_3$ | 19 | 35 | 1.73 |
| H | Cl | H | H | H | $CH_2$ | CO | NH | $CH_3$ | $CH_3$ | 18 | 44 | 2.44 |
| H | H | Cl | H | H | $CH_2$ | CO | NH | $CH_3$ | $CH_3$ | 19 | 44 | 2.31 |
| H | H | F | H | H | $CH_2$ | CO | NH | $CH_3$ | $CH_3$ | 18 | 35 | 1.94 |
| H | H | $CH_3$ | H | H | $CH_2$ | CO | NH | $CH_3$ | $CH_3$ | 18 | 45 | 2.5 |
| H | H | $CF_3$ | H | H | $CH_2$ | CO | NH | $CH_3$ | $CH_3$ | 18 | 42 | 2.33 |
| H | H | OMe | H | H | $CH_2$ | CO | NH | $CH_3$ | $CH_3$ | 18 | 38 | 2.11 |
| H | H | Cl | Cl | H | $CH_2$ | CO | NH | $CH_3$ | $CH_3$ | 18 | 50 | 2.77 |
| H | Me | H | Me | H | $CH_2$ | CO | NH | $CH_3$ | $CH_3$ | 18 | 52 | 2.88 |
| H | H | H | H | H | O | CO | NH | $CH_3$ | $CH_3$ | 18 | 34 | 1.88 |
| H | H | Cl | H | H | O | CO | NH | $CH_3$ | $CH_3$ | 19 | 34 | 1.78 |
| H | H | H | H | H | NH | CO | $CH_2$ | $CH_3$ | $CH_3$ | 19 | 54 | 2.84 |
| H | H | Cl | H | H | NH | CO | $CH_2$ | $CH_3$ | $CH_3$ | 19 | 54 | 2.84 |
| H | Cl | Cl | H | H | NH | CO | $CH_2$ | $CH_3$ | $CH_3$ | 18 | 65 | 3.61 |
| H | Cl | H | Cl | H | NH | CO | $CH_2$ | $CH_3$ | $CH_3$ | 19 | 83 | 4.36 |

TABLE 1-continued

| $R_2$ | $R_3$ | $R_4$ | $R_5$ | $R_6$ | X | Y | Z | $R_7$ | $R_8$ | $P_{50}c$ | $P_{50}$ | $P_{50}/P_{50}c$ |
|---|---|---|---|---|---|---|---|---|---|---|---|---|
| H | Cl | Cl | Cl | H | NH | CO | $CH_2$ | $CH_3$ | $CH_3$ | 19 | 63 | 3.3 |
| H | H | F | H | H | NH | CO | $CH_2$ | $CH_3$ | $CH_3$ | 18 | 45 | 2.5 |
| H | H | $CF_3$ | H | H | NH | CO | $CH_2$ | $CH_3$ | $CH_3$ | 18 | 44 | 2.44 |
| H | H | $CH_3$ | H | H | NH | CO | $CH_2$ | $CH_3$ | $CH_3$ | 18 | 49 | 2.72 |
| H | $CH_3$ | H | $CH_3$ | H | NH | CO | $CH_2$ | $CH_3$ | $CH_3$ | 19 | 75 | 3.94 |
| Cl | H | H | H | Cl | NH | CO | $CH_2$ | $CH_3$ | $CH_3$ | 18 | 34 | 1.89 |
| H | $CH_3$ | $CH_3$ | H | H | NH | CO | $CH_2$ | $CH_3$ | $CH_3$ | 18 | 62 | 3.41 |
| | NAPHTHYL | | | | NH | CO | $CH_2$ | $CH_3$ | $CH_3$ | 18 | 58 | 3.2 |
| H | Cl | H | H | H | NH | CO | $CH_2$ | $CH_3$ | $CH_3$ | 18 | 61 | 3.4 |
| H | H | Cl | H | H | $CH_2$ | NH | CO | $CH_3$ | $CH_3$ | 18 | 27 | 1.5 |
| H | H | $CH_3$ | H | H | $CH_2$ | NH | CO | $CH_3$ | $CH_3$ | 19 | 28 | 1.47 |
| H | Cl | Cl | H | H | $CH_2$ | NH | CO | $CH_3$ | $CH_3$ | 18 | 28 | 1.56 |
| H | H | H | H | H | $CH_2$ | NH | CO | $CH_3$ | $CH_3$ | 19 | 22 | 1.16 |
| | INDANYL | | | | NH | CO | $CH_2$ | $CH_3$ | $CH_3$ | 18 | 64 | 3.56 |
| | ADAMANTYL | | | | NH | CO | $CH_2$ | $CH_3$ | $CH_3$ | 18 | 32 | 1.78 |
| H | $CH_3$ | H | $CH_3$ | H | NH | CO | $CH_2$ | H | $CH(CH_3)_2$ | 19 | 42 | 2.21 |
| H | $CH_3$ | H | $CH_3$ | H | NH | CO | $CH_2$ | H | $CH_2C(CH_3)_2$ | 19 | 38 | 2.0 |
| H | $CH_3$ | H | $CH_3$ | H | NH | CO | $CH_2$ | cyclopentyl | | 19 | 61 | 3.2 |
| H | $CH_3$ | H | $CH_3$ | H | NH | CO | $CH_2$ | cyclohexyl | | 19 | 43 | 2.26 |
| H | $CH_3$ | H | $CH_3$ | H | NH | CO | $CH_2$ | $C_2H_5$ | $C_2H_5$ | 19 | 31 | 1.63 |
| H | Cl | H | Cl | H | NH | CO | $CH_2$ | cyclohexyl | | 19 | 36 | 1.89 |
| H | Cl | H | Cl | H | NH | CO | $CH_2$ | $C_2H_5$ | $C_2H_5$ | 18 | 26 | 1.44 |
| H | H | $CH_3$ | H | H | $SO_2$ | NH | $CH_2$ | $CH_3$ | $CH_3$ | 18 | 35 | 1.94 |
| H | H | Cl | H | H | CO | NH | $(CH_2)_2$ | $CH_3$ | $CH_3$ | 18 | 35 | 1.83(BZF) |

It is noted that the $P_{50}$ control value is less than the $P_{50}$ for normal hemoglobin under physiological conditions (e.g., 26.5) because here the $P_{50}$ was made on hemoglobin in solution (outside the red blood cells). Each hemoglobin sample treated with one of the compounds falling within the family defined by this invention had a $P_{50}$ drug value which was greater than the $P_{50}$ control. This response indicates that the allosteric equilibrium for hemoglobin has been shifted towards favoring the low oxygen affinity "T" state of hemoglobin due to the presence of the compounds.

At the bottom of Table 1, the $P_{50}$ results are presented for bezafibrate (BZF), a known "right-shifting" allosteric hemoglobin modifier. As with all the newly discovered "right-shifting" allosteric hemoglobin modifiers, the hemoglobin treated with BZF had a higher $P_{50}$ than the $P_{50}$ for the control.

Table 1 shows the varying $R_{2-6}$ moieties for the substituted phenyl compounds tested, and when a compound which did not have a substituted phenyl, the name of the compound is written across $R_{2-6}$ (e.g., naphthyl, adamantyl, indanyl). The $R_{7-8}$ moieties were methyl groups for most of the compounds tested; however, data for hydrogen, ethyl, isopropyl, isobutyl, cyclopentyl, and cyclohexyl is also presented in Table 1. Table 1 demonstrates the $R_{7-8}$ moieties may be the same or different and may be hydrogen, halogen, methyl, ethyl, propyl, isopropyl, neopentyl, butyl, substituted or unsubstituted aryl (phenyl, naphthyl, etc.), or alkyl moieties as part of a substituted or unsubstituted aliphatic ring (cyclopropyl, cyclobutyl, cyclopentyl, or cyclohexyl) connecting $R_7$ and $R_8$. The $R_9$ moiety was a sodium cation for each compound tested which is derived from the $NaHCO_3$ treatment prior to testing; however, other salt cations such as ammonia, etc., or esters, ethers, or other derivatives can easily be made within the practice of the invention. Because other compounds within the family would have a similar mode of binding (e.g., those with different $R_{2-9}$ moieties), their effect on the $P_{50}$ value can be expected to be the same. The phthalimide structure defined by FIGS. 12a–b had a mean $P_{50}$ value (e.g., $P_{50}$Drug/$P_{50}$Control) of 1.08 indicating the allosteric equilibrium for hemoglobin had been shifted towards favoring the low oxygen affinity "T" state of hemoglobin by the phthalimide compound.

Table 2 shows the effect some of the compounds on the oxygen dissociation of normal hemoglobin in intact human red blood cells (RBCs).

TABLE 2

| $R_2$ | $R_3$ | $R_4$ | $R_5$ | $R_6$ | X | Y | Z | $R_7$ | $R_8$ | $P_{50}$ |
|---|---|---|---|---|---|---|---|---|---|---|
| | | | | control | | | | | | 27 |
| H | $CH_3$ | H | $CH_3$ | H | NH | CO | $CH_2$ | $CH_3$ | $CH_3$ | 83 |
| H | Cl | H | Cl | H | NH | CO | $CH_2$ | $CH_3$ | $CH_3$ | 87 |
| H | $CH_3$ | H | $CH_3$ | H | NH | CO | $CH_2$ | $CH_3$ | $CH_3$ | 76 |
| H | Cl | H | Cl | H | NH | CO | $CH_2$ | $CH_3$ | $CH_3$ | 68 |

The first entry provides the $P_{50}$ value obtained for a control of human RBCs alone. The next two entries provide the $P_{50}$ values when the RBCs are mixed together with a 10 millimolar (mM) solution of the sodium salt of either 2-[4-((((3,5-diclorophenyl)amino)carbonyl)methyl)phenoxy]-2-methyl propionic acid ($C_{18}H_{17}Cl_2NO_4$) (discussed in Example 10) or 2-[4((((3,5-dimethylphenyl)amino) carbonyl)methyl)phenoxy]-2-methyl propionic acid ($C_{20}H_{23}NO_4$) (discussed in Example 15), respectively. Note that the $P_{50}$ values for the hemoglobin in intact RBCs treated with the compounds is much greater than the $P_{50}$ value for untreated hemoglobin under physiological conditions (e.g., the control=27). In addition, it was determined that the $P_{50}$ value was raised from 27 to 31 in the presence of 1 mM 2-[4((((3,5-dimethylphenyl)amino)carbonyl)methyl) phenoxy]-2-methyl propionic acid and to 42 in the presence of 2 mM 2-[4((((3,5-dimethylphenyl)amino)carbonyl) methyl)phenoxy]-2-methyl propionic acid. This data establishes the permeability of the compounds to the cell membrane and that serum albumin does not interfere with the drug's influence on the oxygen dissociation curve of hemoglobin. The last two entries in Table 2 provide the $P_{50}$ values for intact RBCs treated with 10 mM of the same two compounds, except that the RBCs were washed with a 240 fold excess of 0.9% saline. The relatively slight drop in the $P_{50}$ value after the saline wash, which represents a high retention of allosteric effect, shows that the compounds used in the present invention have high binding affinity for hemoglobin.

Figure 8:
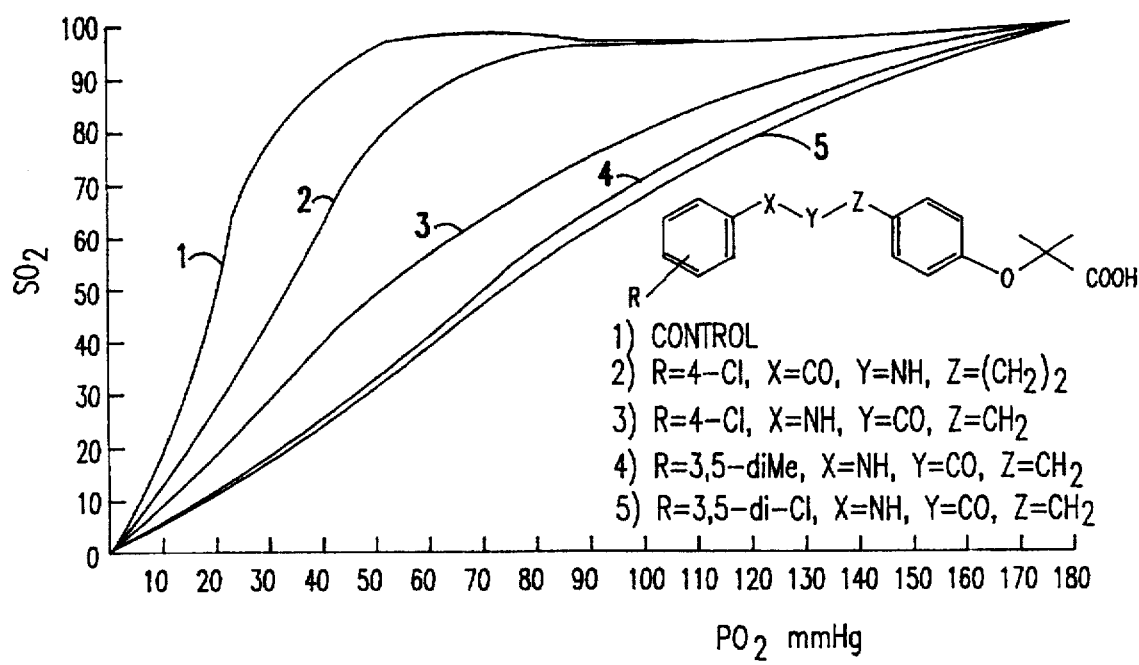
FIG. 8 is a graph illustrating the oxygen dissociation curves produced when a 5.4 millimolar solution of normal hemoglobin in the presence and absence of selected compounds is tested at pH 7.4 using HEPES as the buffer in a Hem-O-Scan oxygen dissociation analyzer.

FIG. 8 is a graph illustrating the oxygen dissociation curves produced when a 5.4 millimolar solution of normal hemoglobin is tested at pH 7.4 using HEPES as the buffer in a Hem-0-Scan oxygen dissociation analyzer. As described above, the $P_{50}$ values reported in Table 1 were determined from curves like those shown in FIG. 8. With particular reference to FIG. 8, the percent oxygen saturation (S $O_2$ on the vertical axis) is plotted against the partial pressure of oxygen (P $O_2$ on the horizontal axis). Curve number 1 shows the oxygen dissociation curve (ODC) in the absence of an allosteric modifying agent. Curve number 2 shows the ODC has been shifted to the right when 10 mM bezafibrate (a known right shifting agent) solubilized with an equimolar amount of $NaHCO_3$ is added to the hemoglobin. It should be noted that as the curve is right shifted to a lower oxygen affinity state, the $P_{50}$ value increases. Curve number 3 shows the right shift caused by adding a 10 mM concentration of 2-[4-((((4-chlorophenyl)amino)carbonyl)methyl)phenoxy]-2-methyl propionic acid ($C_{18}H_{18}ClNO_4$) (described in Example 8 above) to the hemoglobin. Curve number 4 shows the right shift caused by adding a 10 mM concentration of 2-[4-((((3,5-dimethylphenyl)amino)carbonyl) methyl)phenoxy]-2-methyl propionic acid ($C_{20}H_{23}NO_4$) (described in Example 15) to the hemoglobin. Finally, curve number 5 shows the right shift caused by adding a 10 mM concentration of 2-[4-((((3,5-dichlorophenyl)amino) carbonyl)methyl)phenoxy]-2-methyl propionic acid ($C_{18}H_{17}Cl_2NO_4$) (described in Example 10) to the hemoglobin. The right shifting effect shown in FIG. 8 indicates the compounds may be used to lower the oxygen affinity of hemoglobin.

Figure 9:
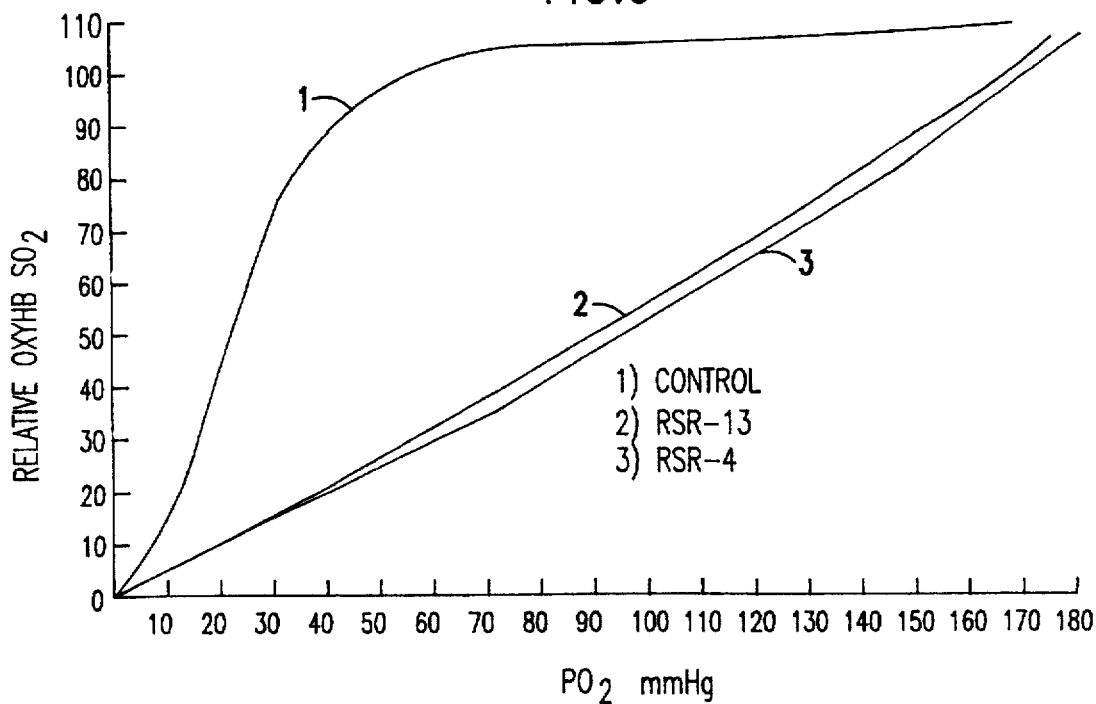
FIG. 9 is a graph similar to FIG. 8 which illustrates oxygen dissociation curves for whole human blood in the presence and absence of selected compounds.

FIG. 9 illustrates the effect of particular compounds on the ODC of whole human blood. Like FIG. 8, the percent oxygen saturation is plotted against the partial pressure of oxygen. As described above, the $P_{50}$ values reported in Table 1 were determined from curves like those shown in FIG. 9. For these curves, 50 μl of whole human blood was mixed with a 50 μl solution of the test compound in HEPES buffer at pH 7.4. Curve number 1 shows the ODC of hemoglobin in unreacted whole blood. Curves 2 and 3 respectively illustrate the right shifting effect of the salts of a 10 mM concentration of 2-[4-((((3,5-dichlorophenyl)amino) carbonyl)methyl)phenoxy]-2-methyl propionic acid ($C_{18}H_{17}Cl_2NO_4$) (described in Example 10 and referred to as RSR-4) or a 10 mM concentration of 2-[4-((((3,5-dimethylphenyl)amino)carbonyl)methyl)phenoxy]-2-methyl propionic acid ($C_{20}H_{23}NO_4$) (described in Example 15 and referred to as RSR-13) on hemoglobin in whole blood.

Figure 10:
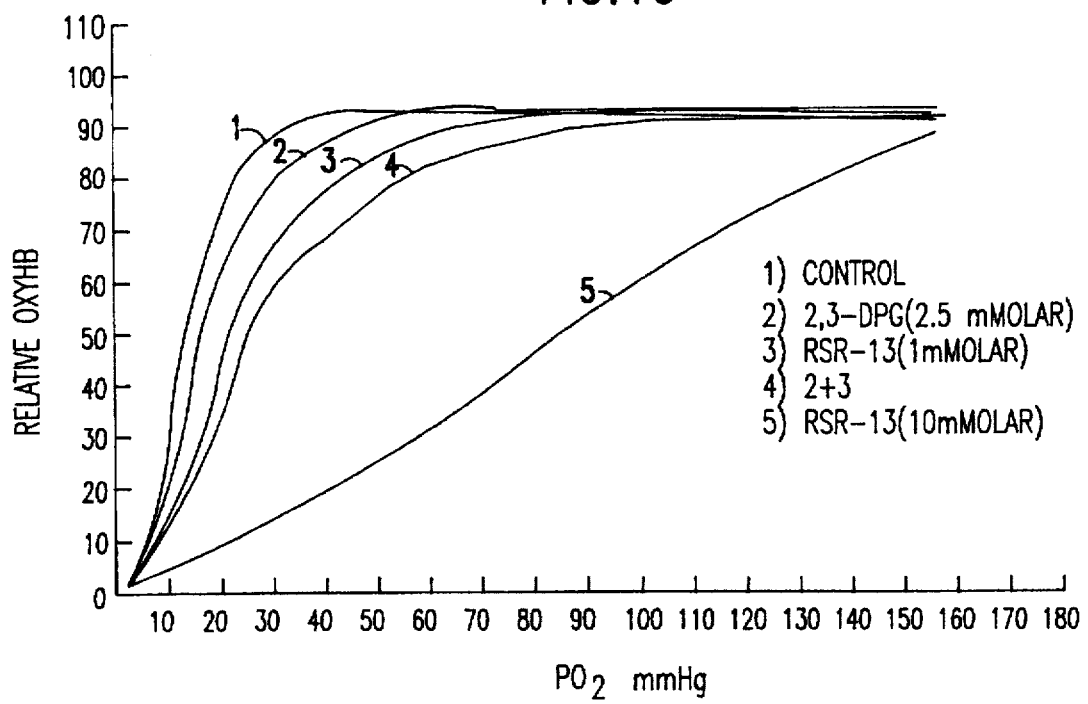
FIG. 10 is a graph similar to FIG. 8 where the oxygen dissociation curves produced are for a 5.4 millimolar solution of normal hemoglobin in the presence and absence of particular compounds, including 2,3-diphosphoglycerate which is the natural allosteric hemoglobin effector, are tested at pH 7.4 using HEPES as the buffer in a Hem-O-Scan oxygen dissociation analyzer.

FIG. 10 shows ODC curves of human hemoglobin (5.4 mM) in HEPES buffer at pH 7.4 which were made in a manner similar to that described in conjunction with FIG. 8. Like FIGS. 8 and 9, the percent oxygen saturation is plotted against the partial pressure of oxygen. Curve number 1 shows ODC of human hemoglobin in the absence of any allosteric modifying agent. Curves 3 and 5 show the right shifting effect of 1 mM and 10 mM concentrations of 2-[4-((((3,5-dimethylphenyl)amino)carbonyl)methyl) phenoxy]-2-methyl propionic acid ($C_{20}H_{23}NO_4$) (described in Example 15 and referred to as RSR-13) on human hemoglobin. Hence, this compound forces hemoglobin to a lower oxygen affinity state. Curve number 2 shows the right shifting effect of 2.5 mM 2,3-diphosphoglycerate (2,3-DPG), which is a natural allosteric hemoglobin effector. Curve number 4 shows the combined effect of two effectors, e.g., 1 mM 2-[4-((((3,5-dimethylphenyl)amino)carbonyl) methyl)phenoxy]-2-methyl propionic acid and 2.5 mM 2,3-DPG, is greater than either effector alone. The synergistic effect may be utilized such that smaller quantities of drugs according to the present invention are added to blood.

Table 3 shows the utility of 2-[4-((((3,5-dimethylphenyl) amino)carbonyl)methyl)phenoxy]-2-methyl propionic acid (called RSR-13) in preserving the oxygen affinity of hemoglobin in stored blood.

TABLE 3

| Packed RBC | $P_{50}$ in presence of RSR-13 | | |
|---|---|---|---|
| Days old | 0 mM | 1 mM | 2 mM |
| Fresh | 38 | — | — |
| 40 | 32 | 39 | 45 |
| 50 | 33 | 39 | 45 |
| 60 | 34 | 40 | 47 |
| 70 | 35 | 39 | 50 |

RSR-13, 1 mM and 2 mM, was added to samples of human RBCs (packed cells) which were stored at 4° C. in standard adsol formulation for 40–70 days. As can be seen from Table 3, the ODC of untreated blood left-shifts over time (indicated by a drop in the $P_{50}$ value) to a high oxygen affinity state. The increase in oxygen affinity of stored blood is attributed to a decreased concentration of 2,3-DPG. The $P_{50}$ value of 40 day old untreated samples left shifted to 32; however, samples treated with 1 mM RSR-13 remained relatively unchanged ($P_{50}$=39) and those treated with 2 mM RSR-13 were right shifted ($P_{50}$=45). Table 3 shows similar concentration dependent effects of RSR-13 on the ODCs of 50, 60, 70 day old packed cells. Because of the glycolytic metabolism, the pH of untreated red cells dropped over a period of time from 6.85 at 40 days to 6.6 for 70 day old samples and this would possibly explain the slight right shifting of untreated 70 day old samples compared to 40 day old samples under the Bohr effect. The pH of red blood cells treated with RSR-13 was consistently lower than untreated samples, which suggests that RSR-13 favorably decreases the rate of glycolytic metabolism. RSR-13 had no adverse effect on the stability of RBCs as evidenced by consistent RBC counts in treated and untreated samples. Similarly, the amount of hemolysis was consistent in both treated and untreated samples of packed cells.

Figure 11:
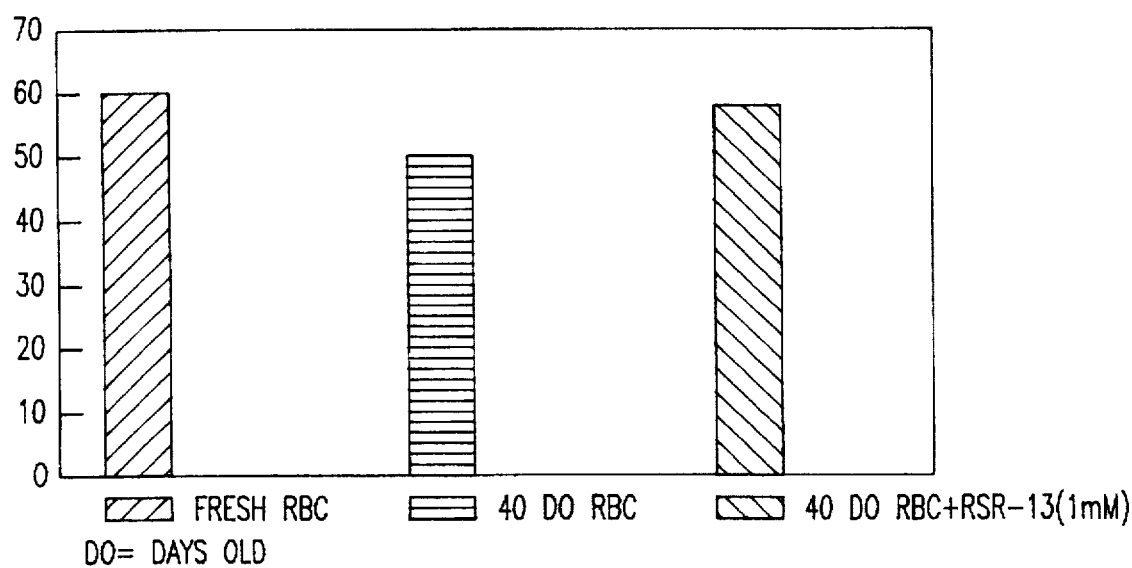
FIG. 11 is a bar graph showing the percentage oxygen delivered by packed cells, fresh, stored and in the presence of 2-[4-((((3,5-dimethylphenyl) amino)carbonyl)methyl) phenoxy]-2-methyl propionic acid ($C_{20}H_{23}NO_4$), respectively.

FIG. 11 shows the percentage oxygen delivered, ΔY, by packed cells. Changes in the oxygen saturation ΔY was calculated by Hill's equation (discussed in Stryer, *Biochemistry*, W. H. Freeman and Co., San Francisco, 1975, Chapter 4, pp. 71–94, which are herein incorporated by reference) at 100 to 30 torr. Column 1 shows the ΔY (59) corresponding to the untreated packed red blood cells. Column 2 shows the ΔY (50) of packed red blood cells stored for 40 days at 4° C. in the best available adsol formulation. Column 3 shows that the ΔY=58 for 40 day old packed cells treated with RSR-13 (1 mM), which is comparable to fresh packed cells. Note, that the decrease (approximately 10%) in the oxygen delivery by packed cells is corrected by the addition of 1 mmol RSR-13.

Table 4 shows the change in the $P_{50}$ values of outdated packed red blood cells on treatment with 2-[4-((((3,5-dimethylphenyl)amino)carbonyl)methyl)phenoxy]-2-methyl propionic acid (RSR-13).

TABLE 4

| Packed RBC | $P_{50}$ in presence of RSR-13 | | |
|---|---|---|---|
| Days old | 0 mM | 1 mM | 2 mM |
| Fresh | 38 | — | — |
| 40 | 32 | 38 | 42 |
| 50 | 31 | 38 | 45 |
| 60 | 34 | 39 | 46 |

50 µl of 40, 50, and 60 day old red cells were mixed with 50 µl of RSR-13 to give final concentrations of RSR-13 at 1 mmol and 2 mmol. Control samples were prepared by mixing 1:1 packed cells and buffer. As can be seen from Table 4, the $P_{50}$ value of untreated samples were consistently lower than samples treated with RSR-13. In addition, a comparison of the results for the fresh red cells with red cells which were aged 40, 50, and 60 days shows a sharp decline in $P_{50}$ value with age. The $P_{50}$ values of 40, 50, 60 day old red cell samples treated with 1 mmol RSR-13 were comparable to the $P_{50}$=38 value found for fresh red cells. These results show that the addition of RSR-13 to the stored red cells restores the cells oxygen affinity.

Figure 13A:
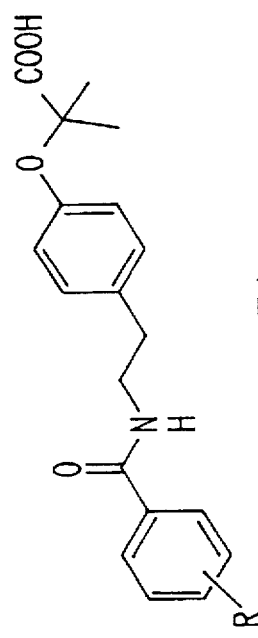
FIGS. 13a and 13b are chemical structures of known antilipidemic agents having allosteric activity, but which are inactive in the presence of physiological levels of serum albumin.
Figure 13B:
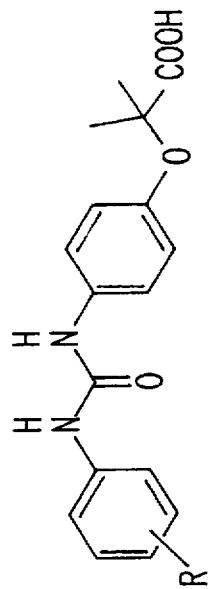

FIG. 13a shows the chemical structure of bezafibrate (BZF). BZF is a known antilipidemic drug which has been shown to decrease the oxygen affinity of blood (see, Perutz et al., *Lancet*, 1983 (881), and Abraham et al., *Proc. Natl. Acad. Sci., USA*, 1983, 80, 324). BZF possesses a four atom chain separting two aromatic units. Lalezari et al., *J. Med. Chem.*, 1989, 32, 2352, have shown that shortening the four atom bridge between the two aromatic rings of BZF to a three atom urea linkage, as is shown in FIG. 13b, results in an increase in allosteric activity. However, the compounds shown in FIGS. 13a and 13b have been shown to be inactive at physiological concentrations of serum albumin.

Modified hemoglobin that gives up oxygen more readily has potential significance in a wide variety of applications including emergency transfusions, in radiosensitization of tumors, in increasing the shelf life of stored blood, and in the treatment of disease states caused by an insufficient supply of oxygen such as ischemia and hypoxia. As discussed above in conjunction with Tables 1–4 and FIGS. 8–11, the compounds of the present invention have been shown to possess allosteric activity in the presence of serum albumin and are, thus, useful clinically. Specifically, the allosteric effectors of this invention have been shown to readily cross the red cell membrane in the presence of serum albumin solutions, restore to normal the oxygen equilibrium curves of outdated blood, shift the oxygen dissociation curves to the right in whole blood and in vivo in rats, and are not inhibited from entering erythrocytes in the presence of the anion channel blocking agent DIDS.

Figure 14A:
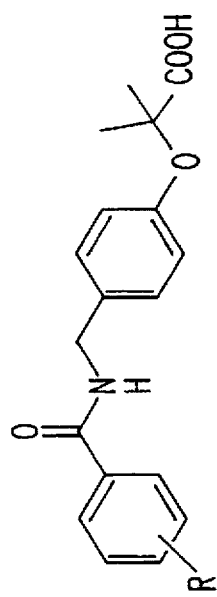
FIGS. 14a–r are chemical structures of several families of allosteric hemoglobin modifiers according to this invention.
Figure 14C:
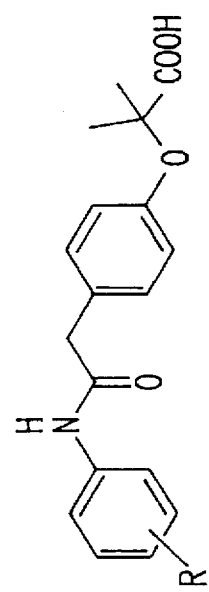
Figure 14B:
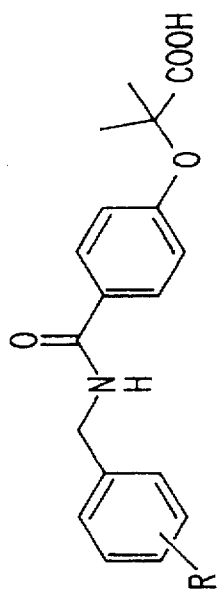
Figure 14D:
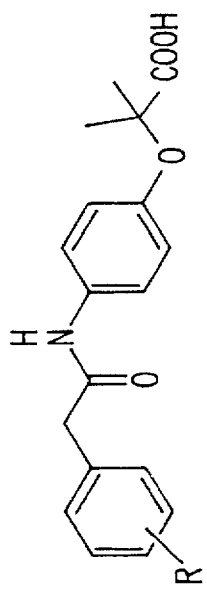
Figure 14F:
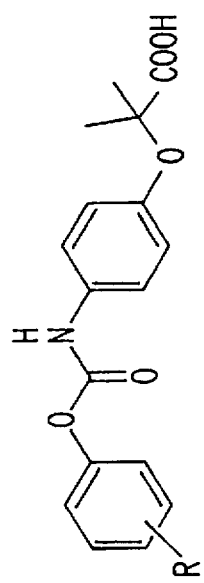
Figure 14H:
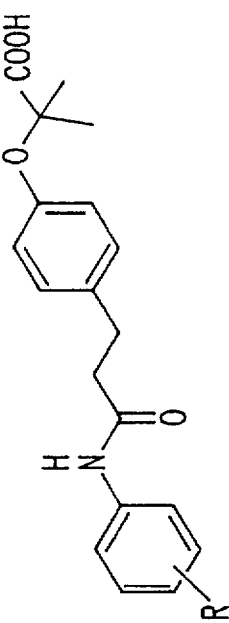
Figure 14J:
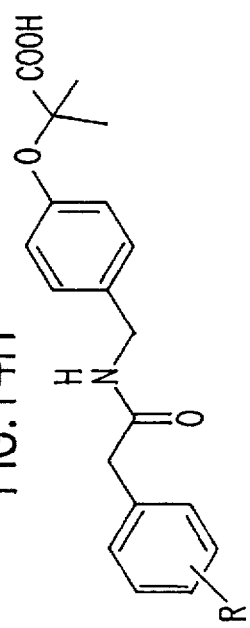
Figure 14L:
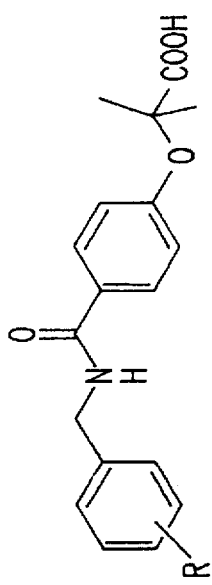
Figure 14E:
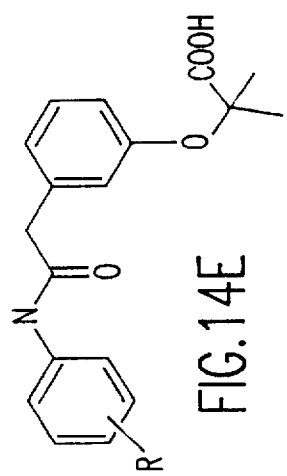
Figure 14G:
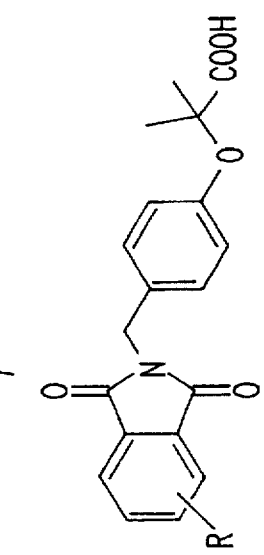
Figure 14I:
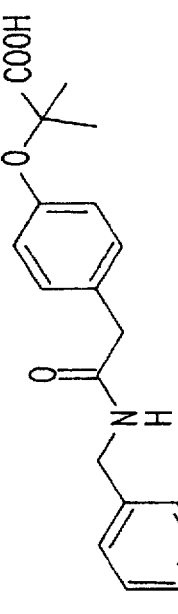
Figure 14K:
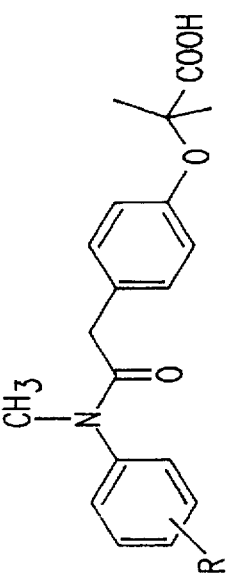
Figure 14N:
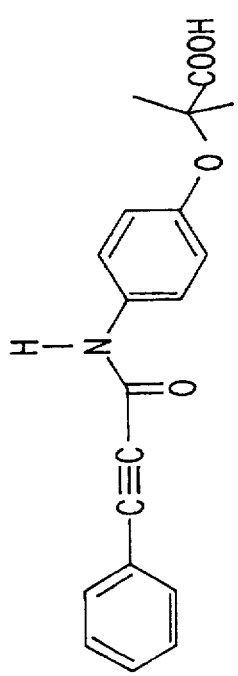
Figure 14P:
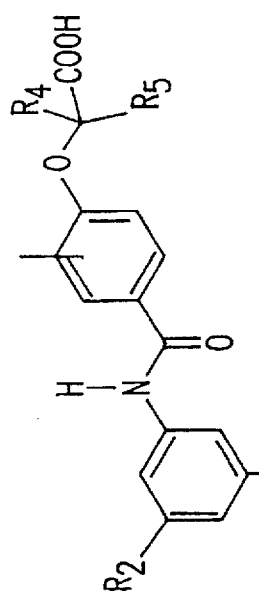
Figure 14R:
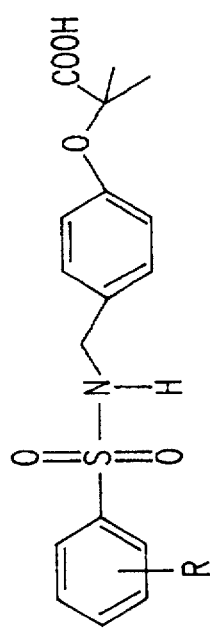
Figure 14M:
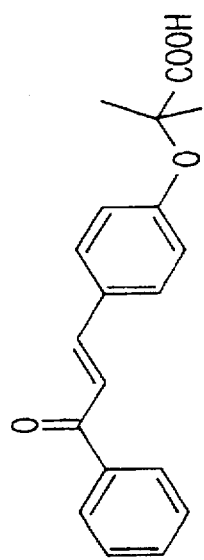
Figure 14O:
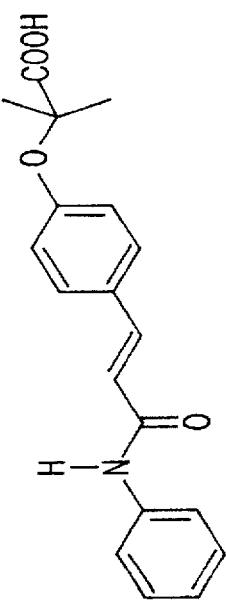

FIGS. 14a-r show generallized chemical structures of several groups of compounds within the practice of this invention which have been synthesized and tested. Contrasting the structures, it can be seen that the central bridge between the aromatic groups have been systematically rearranged, that modifications of the aromatic groups have been made, and that there are differences in substitution on the aromatic groups. For example, FIGS. 14a-e show chemical entities wherein the central bridge includes NH, CO, and $CH_2$ moieties. FIG. 14f shows a chemical entity with O, CO, and $CH_2$ moieties. FIG. 14g shows a chemical entity wherein part of the bridge between the aromatic end groups forms part of a phthalimide compound. FIGS. 14h-j and 14q show chemical entities with a four atom bridge between the aromatics which include NH, CO, and two $CH_2$ moieties. FIG. 14K shows a chemical entity with a central bridge which includes an amide moiety. FIG. 14L shows a chemical entity where one of the aromatic groups is pyridine. FIGS. 14m-o show chemical entities where the central bridge has varying numbers of atoms and where there are varying degrees of unsaturated conjugation (alkenes and alkynes) in the central bridge. FIG. 14p shows a two atom central bridge, and FIG. 14r shows a bridge between the aromatics that includes a sulfur moiety.

All compounds depicted in FIGS. 14a-r, as well as the allostric modifier compounds described above in conjunction with Tables 1–4 and FIGS. 1–7 and 12, fall within a broad family of compounds having the general structure:

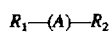

where $R_1$ and $R_2$ each are a substituted or unsubstituted aromatic or heteroaromatic compound, or substituted or unsubsituted alkyl or heteroalkyl ring compound, or a substituted or unsubstituted phthalimide compound, and where $R_1$ and $R_2$ may be the same or different, where A is a chemical bridge which includes two to four chemical moieties bonded together between $R_1$ and $R_2$, wherein said chemical moieties in A are selected from the group consisting of CO, O, S, $SO_2$, NH, $NR_3$ where $R_3$ is a $C_{1-6}$ alkyl group, $NR_4$ where R4 includes two carbonyls as part of a phthalimide compound formed with $R_1$ or $R_2$, $CH_2$, CH, and C, with the caveat that, except in the case where A contains two identical CH and C moieties positioned adjacent one another to form an alkene or alkyne, the chemical moieties in A are each different from one another, and wherein at least one of $R_1$ or $R_2$ is substituted with a compound having the chemical formula:

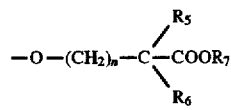

where n is zero to five, where $R_5$ and $R_6$ are selected from the group consisting of hydrogen, halogen, substituted or unsubstituted $C_{1-12}$ alkyl groups, carboxylic acids and esters, substituted or unsubstituted aromatic or heteroaromatic groups, and these moieties may be the same or different, or alkyl moieties of part of an aliphatic ring connecting $R_5$ and $R_6$, and where $R_7$ is a hydrogen, halogen, salt cation, metal, or substituted or unsubstituted $C_{1-6}$ alkyl group.

The protein-bound conformations and the hemoglobin binding sites of the allosteric modifier compounds of this invention were also determined crystallographically. The important interactions of the allosteric modifiers were determined to involve a salt bridge interaction of the acid group with Arg 141 α, a polar interaction of the amide carbonyl with Lys 99 α, and a hydrophobic interaction of the halogenated aromatic ring with Phe 36.

The synthesis pathways for the chemical entities shown in FIGS. 14a and 14b are described above. Examples 34–45 disclose the synthesis of the chemical entities shown in FIGS. 14c-r.

EXAMPLE 34

Figure 15:
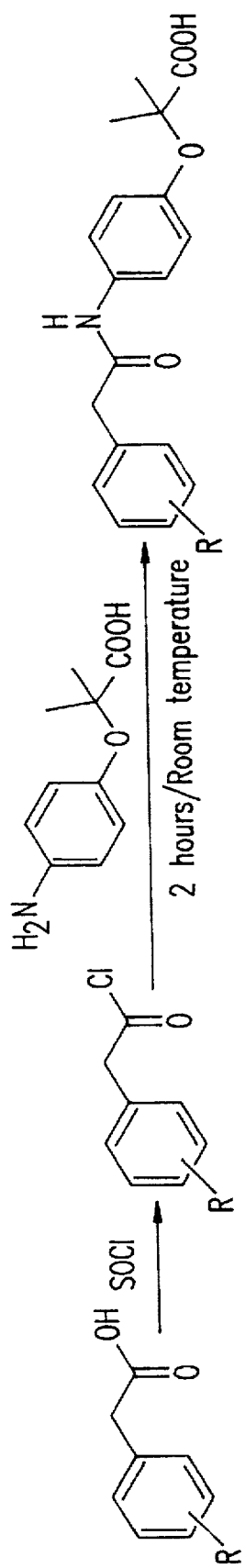
FIG. 15 is a synthetic pathway for preparing the compounds shown in FIG. 14c.

FIG. 15 shows a reaction scheme for preparing the 2[4-(arylacetamido)phenoxy]-2-methylpropionic acid compounds shown in FIG. 14c. The syntheses were accomplished by reaction of the corresponding arylacetylchloride with 2(4-aminophenoxy)-2-methyl propionic acid in the presence of a base. The intermediate 2(4-aminophenoxy)-2-methyl propionic acid was prepared from acetamidophenol.

EXAMPLE 35

Figure 16:
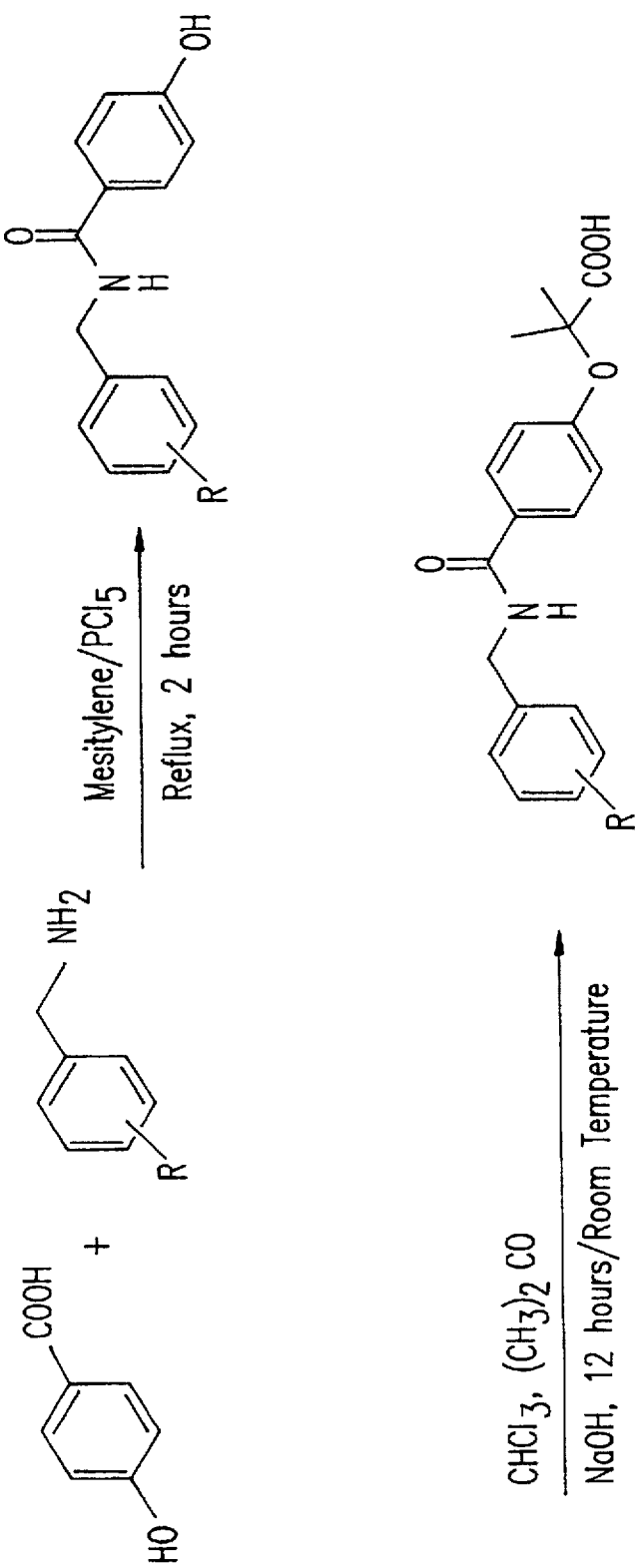
FIG. 16 is a synthetic pathway for preparing the compounds shown in FIG. 14d and 14l.

FIG. 16 shows a reaction scheme for preparing the 2[4-((benzylamino)carbonyl)phenoxy]-2-methylpropionic acids shown in FIG. 14d. The reaction requires suitably substituted benzylamine and 4-hydroxybenzoic acid in the presence of $PCl_5$. The reaction provided the amidophenol in almost quantitative yield. The amidophenol was then converted to an isobutyric acid derivative by treatment with chloroform and acetone in the presence of sodium hydroxide. The compounds of FIG. 14l which include a pyridine heteroaromatic moiety are prepared by a similar process except that a 6-hydroxy 3-nicotinic acid is used instead of 4-hydroxybenzoic acid.

EXAMPLE 36

Figure 17:
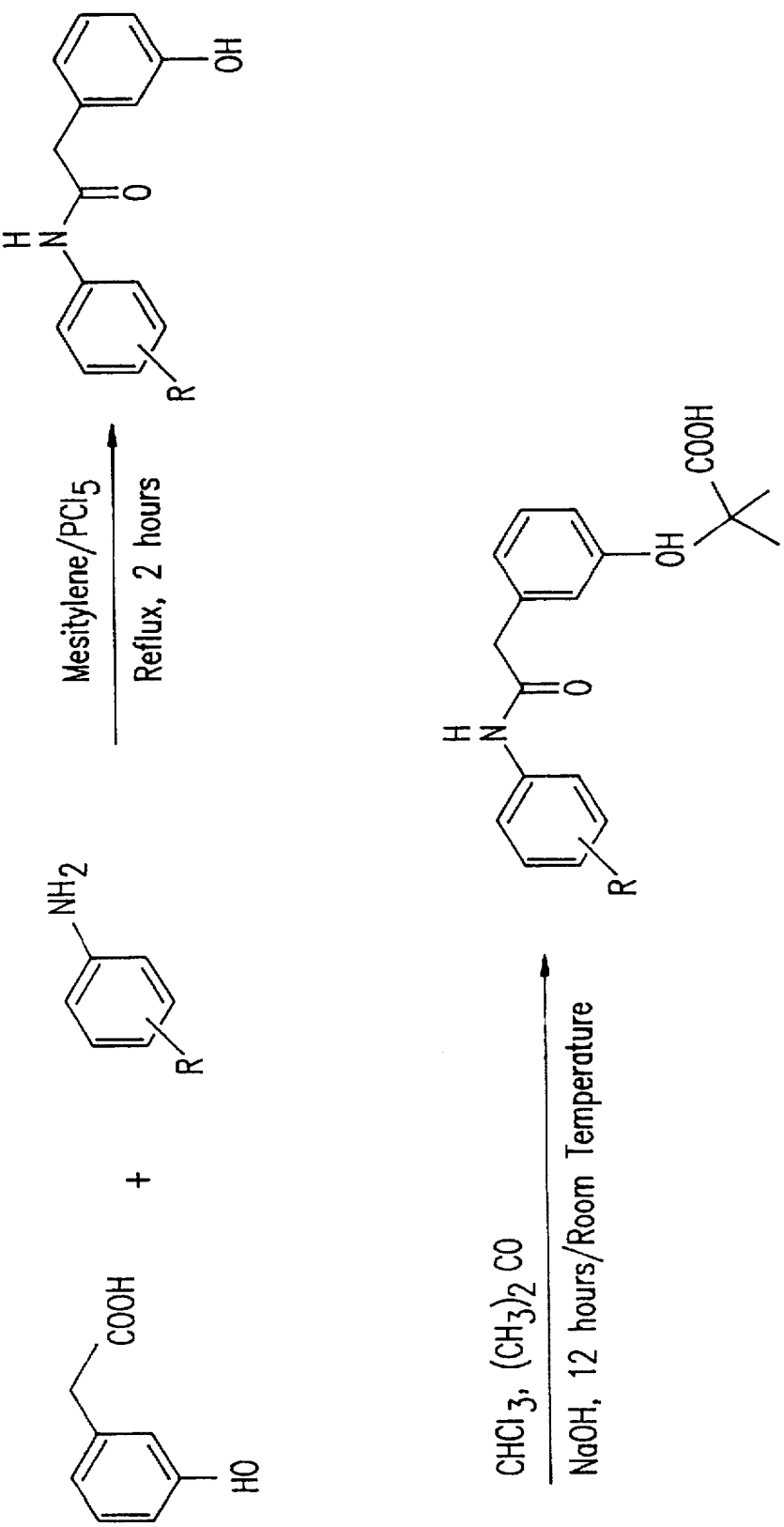
FIG. 17 is a synthetic pathway for preparing the compounds shown in FIG. 14e.

FIG. 17 shows a reaction scheme for preparing the 2[3-(((arylamino)carbonylmethyl)phenoxy-2-methylpropionic acid compounds shown in FIG. 14e. A suitably substituted aniline, 3-hydroxyphenylacetic acid, and $PCl_5$ in mesitylene were refluxed to afford the intermediate amidophenol. The reaction of intermediate amidophenol with $CHCl_3$, acetone, in base afforded the desired isobutyric acid. The analogs of FIGS. 14a and 14k were prepared following a similar procedure as described above, using 4-hydroxyphenylacetic acid and N-methylaniline, respectively.

EXAMPLE 37

Figure 18:
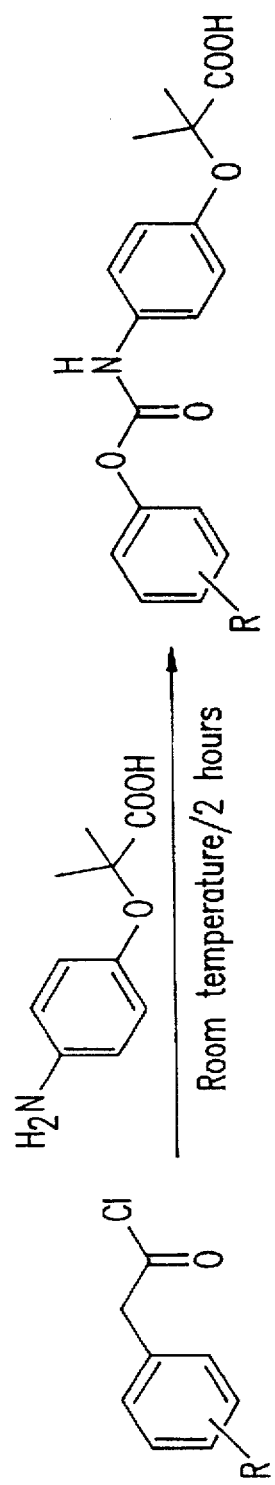
FIG. 18 is a synthetic pathway for preparing the compounds shown in FIG. 14f.

FIG. 18 shows a reaction scheme for preparing the 2[4-((arylacetamido)methyl)phenoxy]-2-methylpropionic acids shown in FIG. 14f. The reaction involved reacting a suitably substituted arylchloroformate with 2[4-aminophenoxy]-2-methylpropionic acid in the presence of base to provide the desired isobutyric acids.

EXAMPLE 38

Figure 19:
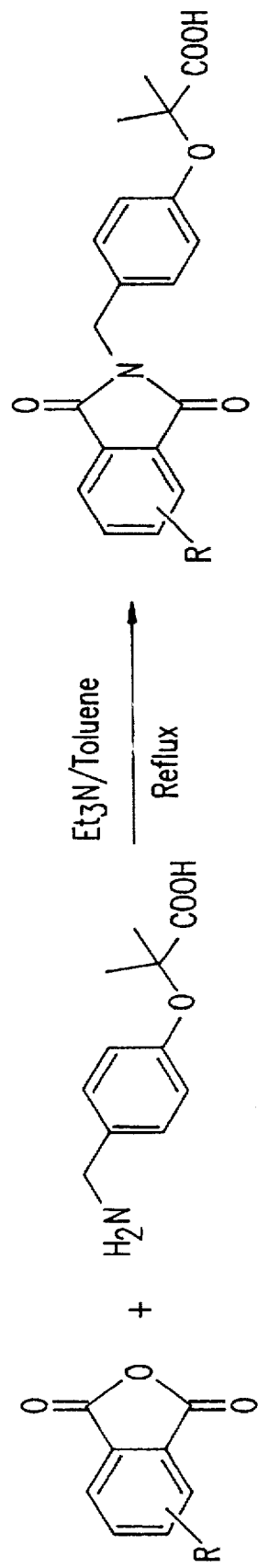
FIG. 19 is a synthetic pathway for preparing the compounds shown in FIG. 14g.

FIG. 19 shows a reaction scheme for preparing the 2-[4-(((phthalamido)N-methyl)phenoxy]-2-methyl propionic acids shown in FIG. 14g. The compound was prepared by refluxing phthalic anhydride and 2[4-((amino)methyl)phenoxy]-2-methylpropionic acid in toluene in the presence of triethylamine. The 2-[4-(((phthalamido)N-methyl)phenoxy]-2-methyl propionic acid was obtained as a crystalline white solid in 90% yield.

EXAMPLE 39

Figure 20:
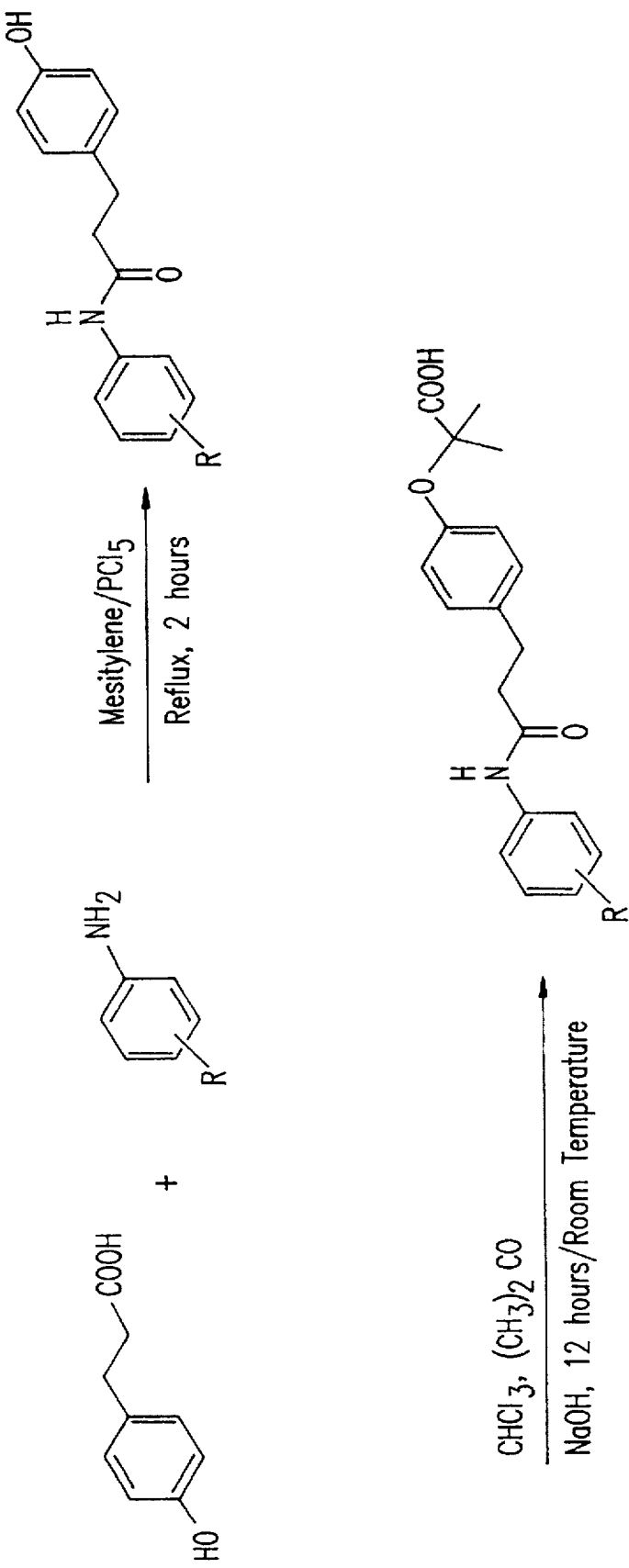
FIG. 20 is a synthetic pathway for preparing the compounds shown in FIG. 14h.
Figure 21:
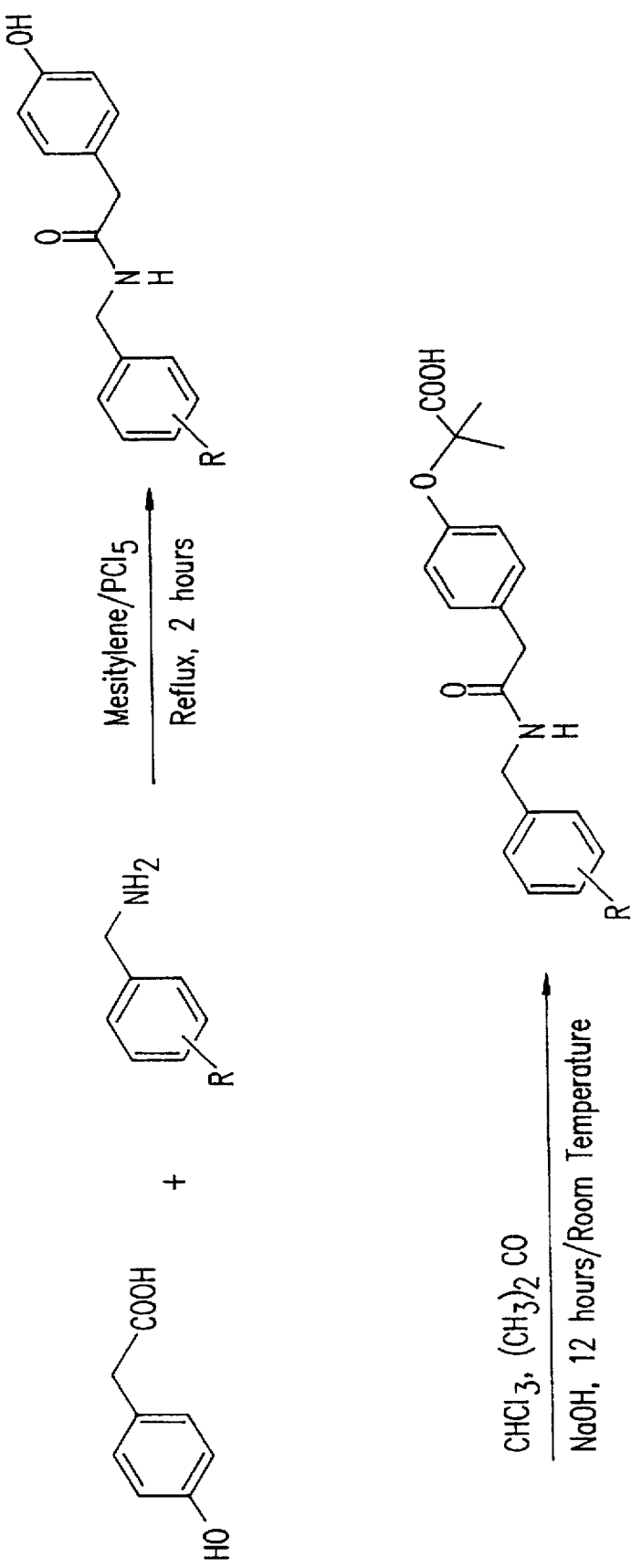
FIG. 21 is a synthetic pathway for preparing the compounds shown in FIG. 14i.

FIG. 20 is a reaction scheme for preparing the 2-[4-(((arylamino)carbonyl)ethyl)phenoxy]-2-methylpropionic acids shown in FIG. 14h. A suitably substituted aniline, 4-hydroxyphenylpropionic acid and $PCl_5$ are refluxed in mesitylene for two hours to furnish the amidophenol. The amidophenol was then converted to the corresponding acid by reaction with acetone, chloroform, and base. The 2-[4-(((benzylamino)carbonyl)methyl)phenoxy]-2-methylpropionic acids of FIG. 14i were prepared by following a similar procedure, as is shown in FIG. 21, but using benzylamine instead of aniline and 4-hydroxyphenylacetic acid instead of 4-hydroxypropionic acid.

EXAMPLE 40

Figure 14Q:
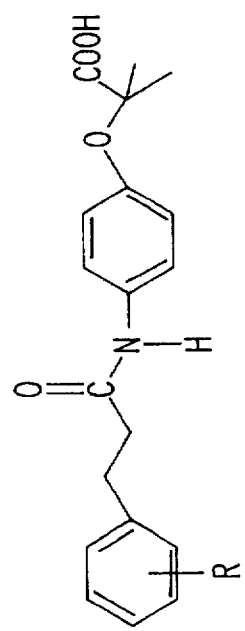
Figure 22A:
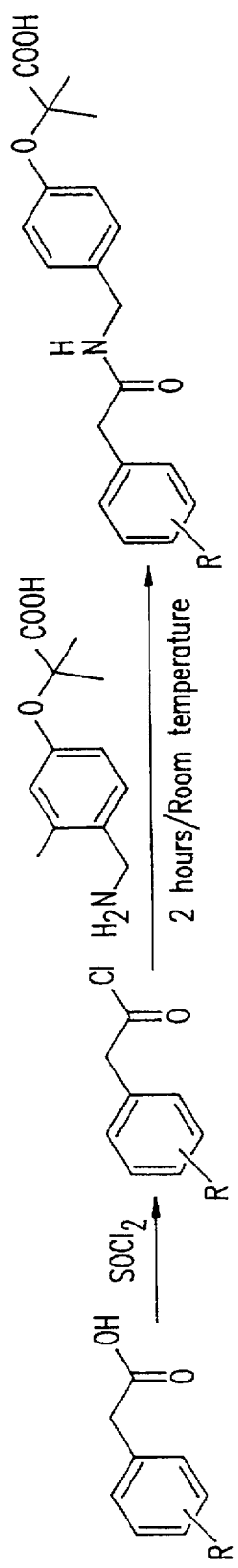
FIGS. 22a–b are synthetic pathways for preparing the compounds shown in FIGS. 14j and 14q.
Figure 22B:
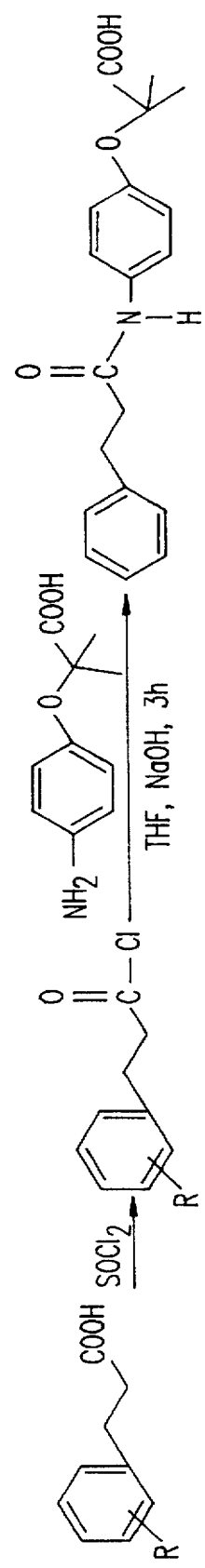

FIG. 22a shows that the reaction of substituted arylacetylchloride with 2-[4-(aminomethyl)phenoxy]-2-methylpropionic acid in the presence of base produces the 2-[4-((arylacetamido)methyl)phenoxy]-2-methylpropionic acid compounds of FIG. 14j. FIG. 22b shows a similar reaction scheme wherein the four atom bridge compound shown as FIG. 14q is prepared. The reaction procedure involves a conversion of a suitably substituted phenylpropionic acid to the corresponding acid chloride by using thionyl chloride in toluene. This acid chloride is then treated at 0° C. with an alkaline (NaOH) solution of 2-[4-aminophenoxy]-2-methylpropionic acid in THF and the reaction mixture is stirred for 2 hrs. Evaporation of THF leads to the recovery of the compound depicted in FIG. 14q.

EXAMPLE 41

Figure 23:
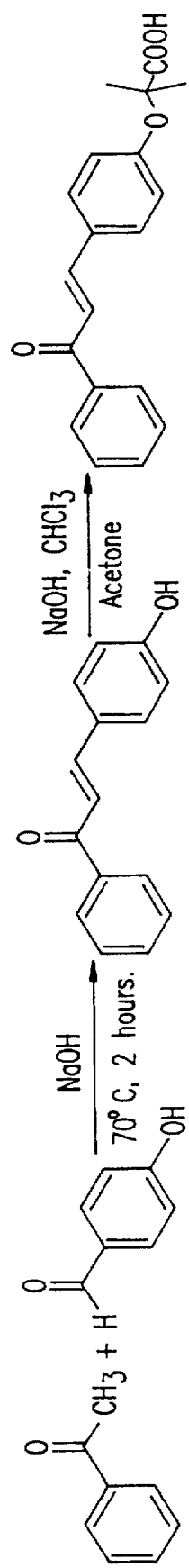
FIG. 23 is a synthetic pathway for preparing the compounds shown in FIG. 14m.

FIG. 23 shows a reaction scheme for preparing the unsaturated conjugated compounds shown in FIG. 14m. A mixture of acetophenone and 4-hydroxybenzaldehyde in ethanol and in the presence of 10% excess sodium hydroxide was heated to 70° C. to produce the intermediate, unsaturated keto alcohol. On treatment with acetone and chloroform in the presence of base, the compound of FIG. 14m resulted.

EXAMPLE 42

Figure 24:
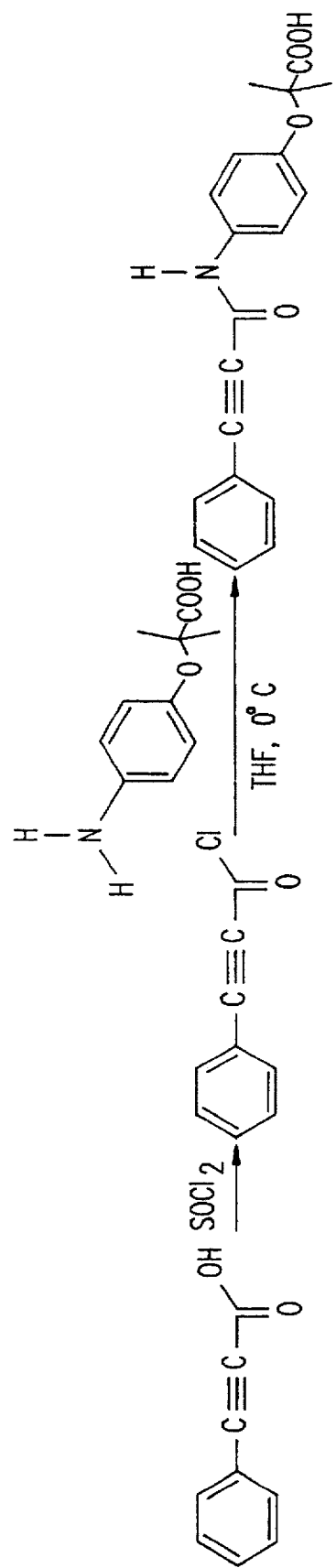
FIG. 24 is a synthetic pathway for preparing the compounds shown in FIG. 14n.

FIG. 24 shows a reaction scheme for preparing the acetylene compounds shown in FIG. 14n. A propiolic acid was converted to its acid chloride by heating it with thionyl chloride. The acid chloride was then treated with 2-[4-(aminophenoxy)-2-methylpropionic acid at 0° C. in the presence of base to produce the compound of FIG. 14n.

EXAMPLE 43

Figure 25:
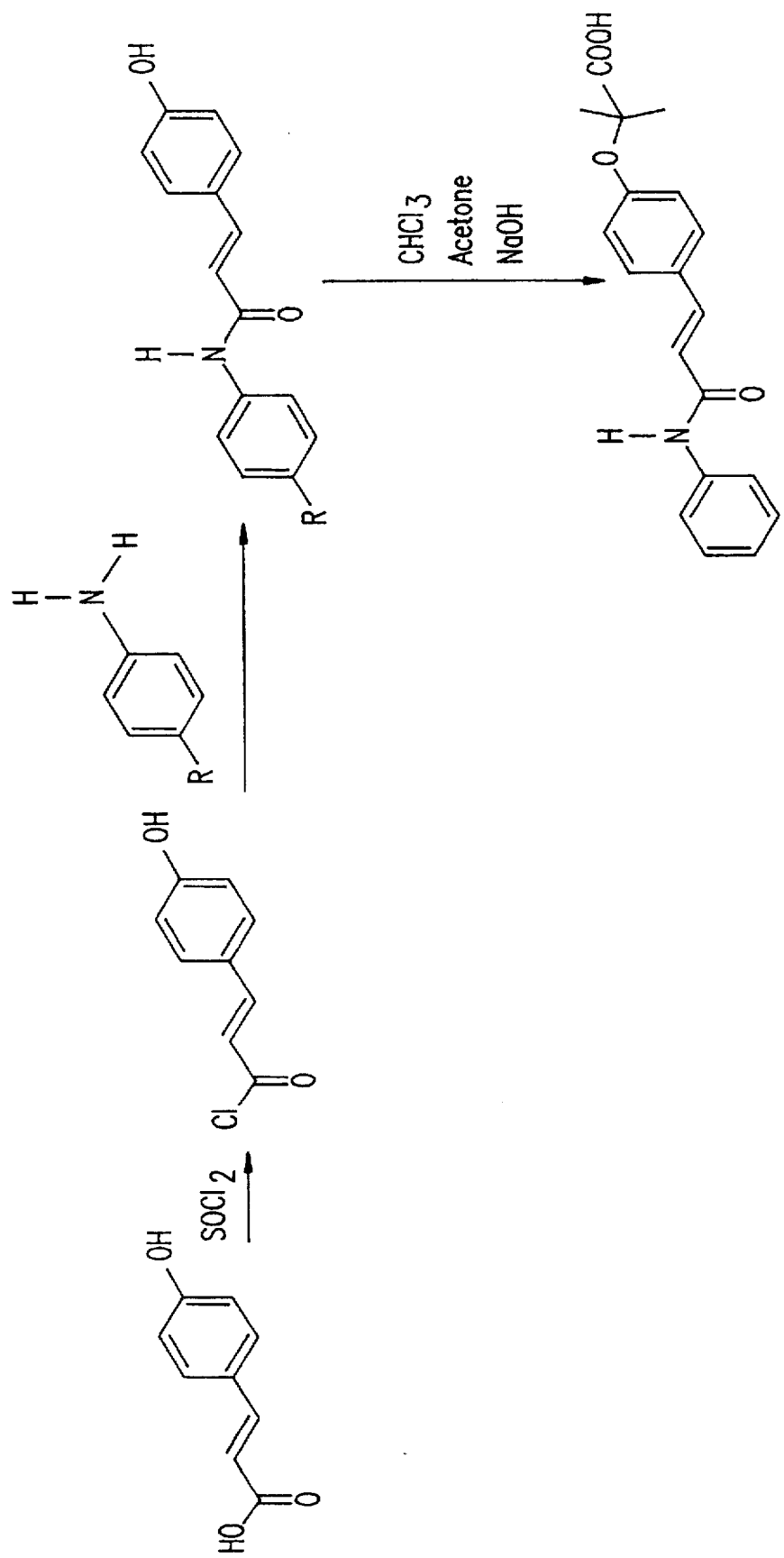
FIG. 25 is a synthetic pathway for preparing the compounds shown in FIG. 14o.

FIG. 25 shows a reaction scheme for preparing the unstaturated conjugated four atom bridge compound shown in FIG. 14o. 4-hydroxycinnamic acid was converted to the acid chloride by using thionyl chloride and then the acid chloride was treated with aniline in p-xylene to produce the intermediate alcohol. The alcohol was converted to the corresponding isobutyric acid derivative shown in FIG. 14o by reaction with acetone, chloroform, and a base.

EXAMPLE 44

Figure 26:
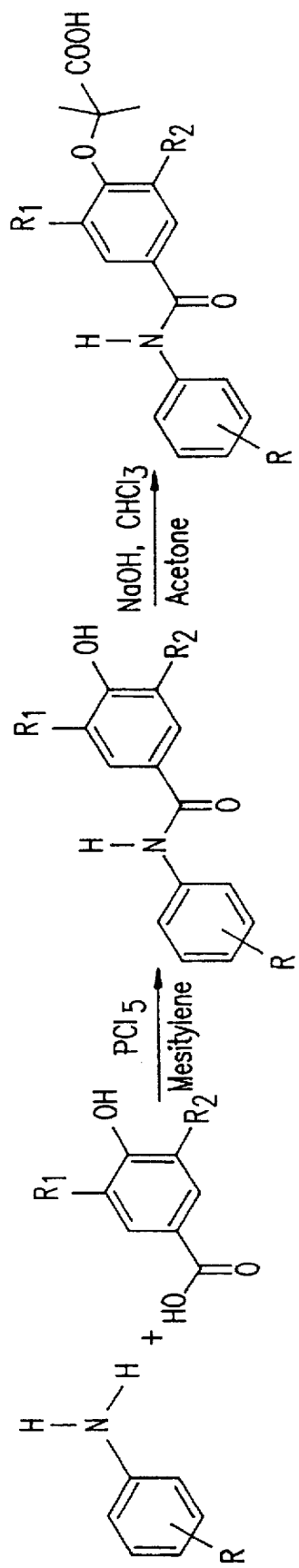
FIG. 26 is a synthetic pathway for preparing the compounds shown in FIG. 14p.

FIG. 26 shows a reaction scheme for preparing the two atom bridge compound shown in FIG. 14p. A mixture of suitably substituted aniline and 4-hydroxybenzoic acid using a catalytic quantity of $PCl_5$ in mesitylene were heated to 140° C. to produce the amidophenol, which was then converted to the corresponding isobutyric acid derivative of FIG. 14p. Similar compounds can be produced by using 3,5-dimethyl-4-hydroxybenzoic acid instead of 4-hydroxybenzoic acid.

EXAMPLE 45

Figure 27:
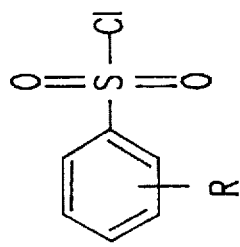
FIG. 27 is a synthetic pathway for preparing the compounds shown in FIG. 14r.
Figure 27:
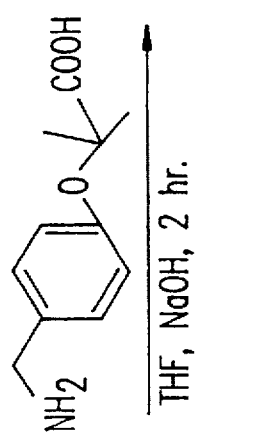
Figure 27:
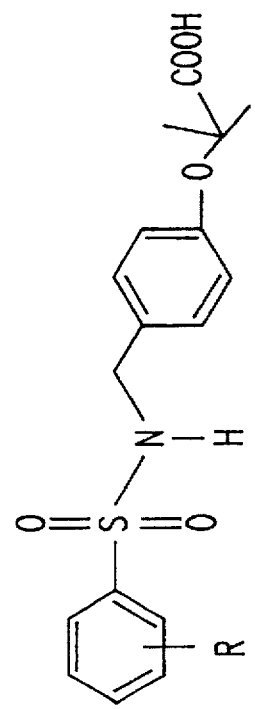

FIG. 27 shows a reaction scheme for preparing the compound shown in FIG. 14r which contains a three atom bridge containing the $-SO_2NHCH_2-$ moiety. This is a one pot reaction involving a suitably substituted aromatic sulphonyl chloride and 2-[4-aminoethylphenoxy]-2-methylpropionic acid. The reaction is generally carried out in THF at 0° C. in the presence of base.

Several compounds which fall within the groups defined by FIGS. 14a–r were tested using a hemoglobin oxygen dissociation analyzer according to the techniques and procedures described above. The compounds exhibited allosteric effector activity by having a demonstrable "right shifting" in the oxygen dissociation curve. Table 5 summarizes the $P_{50}$ data for the new derivatives wherein the $\Delta P_{50}$ represents the difference in the $P_{50}$ measured for sample with analog and the $P_{50}$ for control. Since the shift in $P_{50}$ is dependent on the drug/hemoglobin ratio, all comparisons were performed at a ratio of 4/1 analogue/Hb (i.e., 10 mM analogue/2.7 mM Hb). The high Hb molarity (2.7 mM) used in the oxygen equilibrium studies was intended to approximate the red cell Hb concentration (5 mM). The $P_{50}$ measurements for BZF and the Lalezari compound of FIG. 13b are provided for comparison purposes.

TABLE 5

EFFECT OF ARYLOXY-2-METHYLPROPIONIC ACIDS ON THE OXYGEN AFFINITY OF HEMOGLOBIN

| Compound[a] | $R_2$[b] | $R_3$ | $R_4$ | $R_5$ | $R_6$ | W | X | Y | Z | $\Delta P_{50}$ |
|---|---|---|---|---|---|---|---|---|---|---|
| BZF--13a | H | H | Cl | H | H | CO | NH | $CH_2$ | $CH_2$ | 15 |
| 13b | H | Cl | H | Cl | H |  | NH | CO | NH | 47 |
| 14a (1)[c] | H | Cl | H | Cl | H |  | NH | CO | $CH_2$ | 64 |
| 14a (2) | H | Me[d] | H | Me | H |  | NH | CO | $CH_2$ | 56 |
| 14a (3) | H | Me | H | H | H |  | NH | CO | $CH_2$ | 8 |
| 14a (4) | H | H | OMe | H | H |  | NH | CO | $CH_2$ | 34 |
| 14a (5) | OMe | H | H | H | H |  | NH | CO | $CH_2$ | 32 |
| 14a (6) | H | OMe | H | H | H |  | NH | CO | $CH_2$ | 34 |
| 14a (7) | H | Br | H | H | H |  | NH | CO | $CH_2$ | 24 |
| 14a (8) | H | OMe | OMe | OMe | H |  | NH | CO | $CH_2$ | 39 |
| 14a (9) | H | Me | Me | H | H |  | NH | CO | $CH_2$ | 40 |
| 14a (10) | ADAMANTYL[e] | | | | | | NH | CO | $CH_2$ | 14 |
| 14a (11) | INDANYL[f] | | | | | | NH | CO | $CH_2$ | 46 |
| 14a (12) | NAPHTHYL[g] | | | | | | NH | CO | $CH_2$ | 40 |
| 14k | H | Cl | H | H | H |  | NMe | CO | $CH_2$ | 6 |
| 14b | H | Cl | H | Cl | H |  | CO | NH | $CH_2$ | 29 |
| 14c (1) | H | H | H | H | H |  | $CH_2$ | CO | NH | 16 |
| 14c (2) | H | Cl | H | H | H |  | $CH_2$ | CO | NH | 26 |
| 14c (3) | H | Me | H | H | H |  | $CH_2$ | CO | NH | 27 |
| 14c (4) | H | H | Cl | H | H |  | $CH_2$ | CO | NH | 25 |
| 14c (5) | H | H | F | H | H |  | $CH_2$ | CO | NH | 17 |
| 14c (6) | H | H | Me | H | H |  | $CH_2$ | CO | NH | 27 |
| 14c (7) | H | H | $CF_3$ | H | H |  | $CH_2$ | CO | NH | 24 |
| 14c (8) | H | H | OMe | H | H |  | $CH_2$ | CO | NH | 20 |
| 14c (9) | H | H | Cl | Cl | H |  | $CH_2$ | CO | NH | 32 |
| 14c (10) | H | Me | H | Me | H |  | $CH_2$ | CO | NH | 33 |
| 14d (1) | H | H | H | H | H |  | $CH_2$ | NH | CO | 34 |
| 14d (2) | H | H | Cl | H | H |  | $CH_2$ | NH | CO | 9 |
| 14d (3) | H | H | Me | H | H |  | $CH_2$ | NH | CO | 9 |
| 14d (4) | H | Cl | Cl | H | H |  | $CH_2$ | NH | CO | 10 |
| 14l[h] | H | Cl | H | H | H |  | $CH_2$ | NH | CO | 14 |
| 14f (1) | H | H | H | H | H |  | O | CO | NH | 16 |
| 14f (2) | H | H | Cl | H | H |  | O | CO | NH | 15 |
| 14f (3) | H | H | F | H | H |  | O | CO | NH | 12 |
| 14f (4) | H | H | OMe | H | H |  | O | CO | NH | 11 |
| 14f (5) | H | H | Me | H | H |  | O | CO | NH | 7 |
| 14f (6) | H | H | $NO_2$ | H | H |  | O | CO | NH | 24 |
| 14f (7) | H | Me | H | Me | H |  | O | CO | NH | 8 |
| 14h (1) | H | H | H | H | H | NH | CO | $CH_2$ | $CH_2$ | 10 |
| 14h (2) | H | H | Cl | H | H | NH | CO | $CH_2$ | $CH_2$ | 12 |
| 14i (1) | H | H | H | H | H | $CH_2$ | NH | CO | $CH_2$ | 12 |
| 14i (2) | H | H | Cl | H | H | $CH_2$ | NH | CO | $CH_2$ | 18 |
| 14j (1) | H | H | H | H | H | $CH_2$ | CO | NH | $CH_2$ | 6 |
| 14j (2) | H | H | Me | H | H | $CH_2$ | CO | NH | $CH_2$ | 19 |
| 14n | H | H | H | H | H | C | C | CO | NH | 38 |
| 14o | H | H | Cl | H | H | NH | CO | CH | CH | 12 |
| 14m | H | H | H | H | H |  | CO | CH | CH | 5 |
| 14p (1) | H | H | H | H | H |  |  | NH | CO | 12 |
| 14p (2) | H | Cl | H | Cl | H |  |  | NH | CO | 19 |
| 14p (3) | H | Cl | Cl | H | H |  |  | NH | CO | 14 |
| 14p (4) | H | Cl | Cl | Cl | H |  |  | NH | CO | 18 |
| 14p (5) | H | Me | H | Me | H |  |  | NH | CO | 17 |
| 14p (6) | H | Me | Me | H | H |  |  | NH | CO | 13 |
| 14q (1) | H | H | H | H | H | $CH_2$ | $CH_2$ | CO | NH | 13 |
| 14q (2) | H | H | Cl | H | H | $CH_2$ | $CH_2$ | CO | NH | 12 |
| 14r (1) | H | H | H | H | H |  | $SO_2$ | NH | $CH_2$ | 4 |
| 14r (2) | H | H | Me | H | H |  | $SO_2$ | NH | $CH_2$ | 8 |
| 14r (3) | H | H | Cl | H | H |  | $SO_2$ | NH | $CH_2$ | 11 |
| 14r (4) | H | H | Br | H | H |  | $SO_2$ | NH | $CH_2$ | 9 |
| 14r (5) | H | H | F | H | H |  | $SO_2$ | NH | $CH_2$ | 8 |
| 14r (6) | Cl | H | H | Cl | H |  | $SO_2$ | NH | $CH_2$ | 10 |

[a]Compound identifies structure shown in a particular drawing figure identified by drawing figure number and letter.
[b]R identifies substituents around on the left most aromatic moiety indicated in the drawing.
[c]number in parantheses reflects a variation in the aromatic region where bridge region is identical.
[d]methyl

TABLE 5-continued

EFFECT OF ARYLOXY-2-METHYLPROPIONIC ACIDS ON THE OXYGEN AFFINITY OF HEMOGLOBIN

| Compound[a] | $R_2$[b] | $R_3$ | $R_4$ | $R_5$ | $R_6$ | W | X | Y | Z | $\Delta P_{50}$ |
|---|---|---|---|---|---|---|---|---|---|---|

[a]admantyl moiety present in place of the left most aromatic moiety indicated in the drawing.
[f]Indanyl moiety present in place of the left most aromatic moiety indicated in the drawing.
[g]Naphthyl moiety present present in place of the left most aromatic moiety indicated in the drawing (Naphthyl and phenyls are both aromatic).
[b]right most aromatic is pyridine.

For exemplary purposes FIG. 14P shows substitution on the aromatic ring containing the propionic acid side chain. It should be understood that all of the compounds within the family of compounds defined by this invention can have substitution on the aromatic ring containing the propionic acid side chain and that the propionic acid side chain can be located at any position on the aromatic ring. These compounds are prepared by, for example, using a suitably substituted 4-hydroxybenzoic acid such as 4-hydroxy 3,5-dimethylbenzoic acid or vanillic acid. Table 6 discloses $P_{50}$ data for several different compounds defined by the FIG. 14P structure.

TABLE 6

| $R_2$ | $R_3$ | $R_4$ | $R_5$ | $R_6$ | $R_7$ | $R_8$ | $R_9$ | $R_{10}$ | $\Delta P_{50}$ |
|---|---|---|---|---|---|---|---|---|---|
| H | $CH_3$ | H | $CH_3$ | H | H | $CH_3$ | $CH_3$ | H | 19 |
| H | Cl | H | Cl | H | H | $CH_3$ | $CH_3$ | H | 23 |
| H | $CH_3$ | H | $CH_3$ | H | H | $OCH_3$ | H | H | 21 |

While many of the compounds described above include a propionic acid side chain on one of the aromatic compounds, the side chain can be varied to include halogens, $C_{1-12}$ alkyl groups, substituted and unsubsituted aromatic and heteroaromatic groups, or aliphatic ring groups. Examples 29–32, above, set forth specific synthesis routes for obtaining these types of compounds. Table 7 presents the $P_{50}$ data for several compounds which have been synthesized that have the general structural formula:

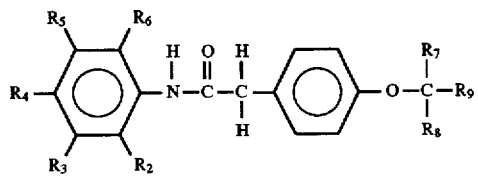

TABLE 7

| $R_2$ | $R_3$ | $R_4$ | $R_5$ | $R_6$ | $R_7$ | $R_8$ | $R_9$ | $\Delta P_{50}$ |
|---|---|---|---|---|---|---|---|---|
| H | $CH_3$ | H | $CH_3$ | H | $CH_2CH_3$ | $CH_2CH_3$ | COOH | 18 |
| H | Cl | H | Cl | H | $CH_2CH_3$ | $CH_2CH_3$ | COOH | 12 |
| H | $CH_3$ | H | $CH_3$ | H | H | H | COOH | 3 |
| H | Cl | H | Cl | H | H | H | COOH | −1 |
| H | $CH_3$ | H | $CH_3$ | H | H | $CH(CH_3)_2$ | COOH | 24 |
| H | $CH_3$ | H | $CH_3$ | H | H | $CH_2C(CH_3)_3$ | COOH | 19 |
| H | $CH_3$ | H | $CH_3$ | H | CYCLOBUTYL[a] | | COOH | 27 |
| H | $CH_3$ | H | $CH_3$ | H | CYCLOPENTYL | | COOH | 42 |
| H | Cl | H | Cl | H | CYCLOPENTYL | | COOH | 11 |
| H | $CH_3$ | H | $CH_3$ | H | CYCLOHEXYL | | COOH | 24 |
| H | Cl | H | Cl | H | CYCLOHEXYL | | COOH | 17 |
| H | $CH_3$ | H | $CH_3$ | H | $CH_3$ | $CH_2CH_3$ | COOH | 24 |
| H | Cl | H | Cl | H | $CH_3$ | $CH_2CH_3$ | COOH | 17 |
| H | $CH_3$ | H | $CH_3$ | H | $CH_3$ | $COOCH_2CH_3$ | $COOCH_2CH_3$ | 1 |
| H | $CH_3$ | H | $CH_3$ | H | $CH_3$ | $COOCH_2CH_3$ | COOH | 3 |
| H | $CH_3$ | H | $CH_3$ | H | $CH_3$ | COOH | COOH | 4 |

[a]Ring structure connecting $R_7$ and $R_8$.

Since the compounds contemplated by this invention are capable of allosterically modifying hemoglobin so that a low oxygen affinity "T" state is favored (right shifting the equilibrium curve), these compounds will be useful in treating a variety of disease states in mammals including humans where tissues suffer from low oxygen tension, such as cancer and ischemia. As pointed out by Hirst et al. in *Radiat. Res.*, Vol. 112, (1987), pp. 164, decreasing the oxygen affinity of hemoglobin in circulating blood has been shown to be beneficial in the radiotherapy of tumors. The compounds may be administered to patients in whom the affinity of hemoglobin for oxygen is abnormally high. Particular conditions include certain hemoglobinopathies and certain respiratory distress syndromes including respiratory distress syndromes in new born infants aggravated by high fetal hemoglobin levels and when the availability of hemoglobin/oxygen to the tissues is decreased (e.g., in ischemic conditions such as peripheral vascular disease, coronary occlusion, cerebral vascular accidents, or tissue transplant). The compounds may also be used to inhibit platelet aggregation and may be used for antithrombotic purposes and wound healing. Topical application could be used for wound healing. In addition, the compounds may be used to treat low oxygen related disorders in the brain such as Alzheimer's disease, depression, and schizophrenia. It may be desirable to administer the compounds to a patient prior to and/or simultaneously with the transfusion of the treated whole blood or red blood cells in order to avoid substantial variations in the hemoglobin oxygen affinity due to dilution that occurs when the blood is administered.

The compounds can be added to whole blood or packed cells preferably at the time of storage or at the time of transfusion in order to facilitate the dissociation of oxygen from hemoglobin and improve the oxygen delivering capability of the blood. Preferably, the compounds would be added in an amount of about 50 mg to 1 g per unit of blood (473 ml) or unit of packed cells (235 ml). When blood is stored, the hemoglobin in the blood tends to increase its affinity for oxygen by losing 2,3-diphosphoglycerides. As described above, the compounds of this invention are capable of reversing and/or preventing the functional abnormality of hemoglobin which is observed when whole blood or packed cells are stored. The compounds may be added to whole blood or red blood cell fractions in a closed system using an appropriate reservoir in which the compound is placed prior to storage or which is present in the anticoagulating solution in the blood collecting bag.

Administration to a patient can be achieved orally, by intravenous or intraperitoneal injection, or rectally by suppository where the dose and the dosing regiment is varied according to individual sensitivity and the type of disease state being treated.

Studies with mice have shown that a mg/kg/day dose of 2-[4((((3,5-dimethylphenyl)amino)carbonyl)methyl)phenoxy]-2-methyl propionic acid ($C_{20}H_{23}NO_4$) (discussed in Example 15 (RSR-13)) given intraperitoneally is well tolerated. In vivo experiments with rodents have also shown that (1) i.v. infusion of RSR 13 results in a decrease in cardiac output and regional flows which indicates that an isolated increase in tissue oxygen delivery may increase total and regional vascular resistance, (2) in the rodent model of focal cerebral ischemia, administration of RSR-13 results in reductions in the volume of infarction, and (3) in rodent experiments done with middle cerebral artery occlusion, the administration of RSR-13 decreased infart size.

If the compounds are used for wound healing, the compounds could advantageously be applied topically directly to the wound area. In addition, the compounds can be mixed with blood external to a patient's body prior to and/or simultaneously with a transfusion. The compounds can be administered in the pure form or in a pharmaceutically acceptable formulation including suitable elixirs, binders, and the like or as pharmaceutically acceptable salts (lithium, soidum, potassium, ammonium, alkaline metals, etc.) or other derivatives (esters, ethers, etc.). It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Solid diluents and excipients include lactose starch, conventional disintegrating agents, coatings and the like.

The following Examples discuss particular uses and administration routes for the allosteric hemoglobine modifiers of this invention.

EXAMPLE 46

Radiation Oncology. Solid tumors are oxygen deficient masses. The allosteric effectors of this invention deliver more oxygen to tumors, which increases radical formation that increases tumor killing during radiation. In animal experiments, transplanted tumors (FSa-II fibrosarcoma tumor of C3H mice) were injected with the allosteric effector and 30–60 minutes later they were exposed to 5–6 Gy of radiation. The process was repeated for five consecutive days. Tumors were measured for regrowth delay and then excised to obtain viable single cells that were plated for clonogenic survival in vitro. The tests in mice show that the allosteric effector RSR-13 increases growth delay of irradiated tumors by 50%.

EXAMPLE 47

Hypothermia limiting or preventing hypoxia induced irreversible myocardial damage. The allosteric effectors increase the efficiency of oxygen delivery at low blood flow and low temperatures, thus having the ability to prevent myocardial damage.

EXAMPLE 48

Resuscitation from hemorrhagic shock. The allosteric effectors may decrease the number of red blood cells required for treating hemorrhagic shock by increasing their efficiency of oxygen delivery.

EXAMPLE 49

Wound Healing, diabetic ulcers, chronic leg ulcers, pressure sores, tissue transplants. Experiments have shown that the allosteric effectors delivery of oxygen to wound healing is important. Damaged tissues heal faster when there is better blood flow and increased oxygen tension. In addition, by increasing oxygen delivery to wounded tissue, the allosteric effectors may play a role in the destruction of infection causing bacteria.

EXAMPLE 50

Stroke. The allosteric effectors will be effective in delivering oxygen to the brain, especially before complete occlusion and reperfusion injuries occur due to free radical formation. In animal experiments, approximately 30% reductions in the volume of infarction result after the administration of RSR-13. The reduction in infarct area obtained in the animal studies reduces concerns about free radical damage from increased oxygen delivery in vivo to ischemic brain tissue.

In addition, animal studies have been conducted where the efficacy of the allosteric effectors in cat brains was assessed by measuring the diameter of small and large arterioles through cranial windows under hypoxic and hypotensive conditions. The studies show that the infusion of the allosteric effectors of this invention reduces the expansion of arterioles to nearer normal controls under both hypoxic and hypotensive conditions.

EXAMPLE 51

Cardiovascular/Angina applications. The allosteric effectors of this invention should be capable of increased oxygen delivery to blocked arteries and surrounding muscles and tissues, thus relieving the distress of angina attacks. The compounds may serve as antithrombolytic agents and decrease fibrinogen.

EXAMPLE 52

Alzheimer's Disease. One of the many symptoms of Alzheimer's disease is decreased flow of oxygen to the brain. The allosteric effectors concentrate in red blood cells which allows enhanced delivery of oxygen to all areas of the body, including the brain. Thus, the allosteric effectors of the present invention can be used to combat the symptom of decreased oxygen flow to the brain and the resulting deterioration of the brain.

EXAMPLE 53

Acute Respiratory Disease Syndrome (ARDS). ARDS is characterized by interstitial and/or alveolar edema and hemorrhage as well as perivascular lung edema associated with hyaline membrane, proliferation of collagen fibers, and swollen epithelium with increased pinocytosis. The enhanced oxygen delivering capacity attributable to the allosteric effectors of this invention can be used in the treatment and prevention of ARDS by combatting lower than normal oxygen delivery to the lungs.

EXAMPLE 54

Use of allosteric effectors with micelles or for use with underwater exploration. Micelles are synthetic lipophylic membrane like spheres that are being intensively investigated for in vivo administration of biological materials. Soya lecithin is a common agent used in creating micelles within a fluid. The micelles protect encapsulated drugs or biological materials from undesired metabolism, antibody detection, etc. Addition of the allosteric hemoglobin modifiers of this invention to micelles which encapsulate hemoglobin will increase the delivery of oxygen to tissues. Since the allosteric effectors of this invention concentrate in erythrocytes when administered in vivo in rats, incorporation of the allosteric effectors in a micelle which encapsulates hemoglobin allows the effector to remain securely within the micelle until it has been degraded. In addition, because of the increased delivery of oxygen attributed to the allosteric effectors of this invention, the allosteric effectors can be used to increase the dive time for underwater divers.

EXAMPLE 55

The in vivo effects on hemoglobin-oxygen (Hb-$O_2$) affinity and tissue $PO_2$ were investigated after intraperitoneal administration of 2-[4-(((dichloroanilino)carbonyl)methyl) phenoxyl]-2-methyl propionic acid (RSR-4; 150 mg/kg) or its 3, 5-dimethyl derivative (RSR 13; 300 mg/kg) in C3Hf/Sed mice. The Hb-$O_2$ dissociation curve was plotted from tail vein blood samples using an $O_2$ dissociation analyzer prior to and up to 160 minutes after compound administration. Twenty to forty minutes after injection, the hemoglobin $P_{50}$ increased by a mean 25% (range 18–31%) after RSR 4 and 53% (range 36–76%) after RSR 13. Tissue $PO_2$ increased by a mean of 78% (range 30–127%) after RSR 4 and 66% (range 39–97%) after RSR 13 administration in anesthetized mice. No change was observed in tissue $PO_2$ in anesthetized controls.

While the invention has been described in terms of its preferred embodiments, those skilled in the art will recognize that the invention can be practiced with modification within the spirit and scope of the appended claims.

We claim:

1. A compound of the general structural formula:

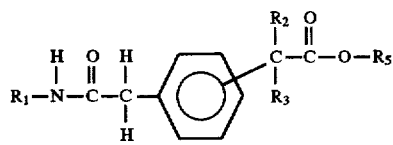

where $R_1$ is selected from the group consisting of optionally substituted phenyl, adamantyl, naphthyl, and indanyl;

where $R_2$ and $R_3$ are alkyl moieties of a $C_{3-6}$ alkyl ring connecting $R_2$ and $R_3$; and where $R_5$ is selected from the group consisting of hydrogen, $C_{1-3}$ lower alkyl, and a monovalent salt cation.

2. The compound of claim 1 wherein $R_1$ is a substituted or unsubstituted phenyl.

3. The compound of claim 1 wherein $R_1$ is a substituted or unsubstituted indanyl.

4. The compound of claim 1 wherein $R_1$ is a substituted or unsubstituted adamantyl.

5. The compound of claim 1 wherein $R_1$ is a substituted or unsubsituted naphthyl.

6. The compound of claim 1 wherein $R_2$ and $R_3$ are alkyl moieties of a $C_5$ alkyl ring connecting $R_2$ and $R_3$.

7. The compound of claim 1 wherein $R_2$ and $R_3$ are alkyl moieties of a $C_6$ alkyl ring connecting $R_2$ and $R_3$.

8. The compound of claim 1 wherein $R_2$ and $R_3$ are alkyl moieties of a $C_4$ alkyl ring connecting $R_2$ and $R_3$.

9. The compound of claim 1 where the moiety containing $R_2$, $R_3$ and $R_5$ grooves are connected at the para position of the phenyl ring.

10. The compound of claim 9 where $R_1$ is substituted with a substituent selected from the group consisting of halogens, $NO_2$, $C_{1-3}$ alkyl, halogenated $C_{1-3}$ alkyl, $C_{1-3}$ ether, and $C_{1-3}$ carboxylic acid ester.

UNITED STATES PATENT AND TRADEMARK OFFICE
CERTIFICATE OF CORRECTION

PATENT NO.: 5,731,454

DATED: March 24, 1998

INVENTOR(S): Abraham et al.

It is certified that error appears in the above-identified patent and that said Letters Patent is hereby corrected as shown below:

In claim 1, remove the formula that appears in lines 25-30 of column 32 and insert:

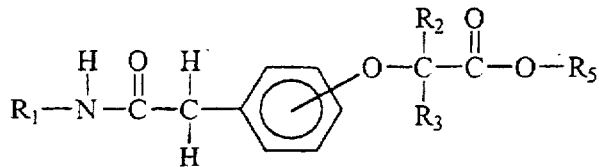

Signed and Sealed this

Twenty-seventh Day of June, 2000

Attest:

Q. TODD DICKINSON

Attesting Officer

Director of Patents and Trademarks